(12) United States Patent
Karc

(10) Patent No.: US 10,751,570 B2
(45) Date of Patent: Aug. 25, 2020

(54) ATHLETIC SPEED AND TIME MEASUREMENT DEVICE AND METHODS OF MAKING AND USING SAME

(71) Applicant: Jeffrey J. Karc, Danielsville, PA (US)

(72) Inventor: Jeffrey J. Karc, Danielsville, PA (US)

(*) Notice: Subject to any disclaimer, the term of this patent is extended or adjusted under 35 U.S.C. 154(b) by 0 days.

(21) Appl. No.: 16/045,429

(22) Filed: Jul. 25, 2018

(65) Prior Publication Data

US 2019/0030396 A1 Jan. 31, 2019

Related U.S. Application Data

(63) Continuation-in-part of application No. 62/537,409, filed on Jul. 26, 2017.

(51) Int. Cl.
| | |
|---|---|
| *A63B 69/00* | (2006.01) |
| *A63B 24/00* | (2006.01) |
| *G06K 9/00* | (2006.01) |
| *A61B 5/11* | (2006.01) |
| *A61B 5/00* | (2006.01) |
| *G09B 19/00* | (2006.01) |

(52) U.S. Cl.
CPC ............ *A63B 24/0021* (2013.01); *A61B 5/11* (2013.01); *A61B 5/6895* (2013.01); *A63B 69/0002* (2013.01); *A63B 69/0013* (2013.01); *G06K 9/00342* (2013.01); *G06K 9/00496* (2013.01); *A61B 5/1114* (2013.01); *A61B 5/6892* (2013.01); *A61B 2503/10* (2013.01); *A61B 2562/0204* (2013.01); *A61B 2562/0219* (2013.01); *A63B 2024/0025* (2013.01); *A63B 2024/0056* (2013.01); *A63B 2069/0004* (2013.01); *G09B 19/0038* (2013.01)

(58) Field of Classification Search
CPC ............ A63B 69/0002; A63B 69/0004; A63B 69/0008; A63B 69/0013
See application file for complete search history.

(56) References Cited

U.S. PATENT DOCUMENTS

| | | |
|---|---|---|
| 3,363,243 A | 1/1968 | Morley |
| 4,194,101 A | 3/1980 | Berseth |
| 4,627,620 A | 12/1986 | Yang |

(Continued)

FOREIGN PATENT DOCUMENTS

CN 205608825 4/2016

*Primary Examiner* — Steven J Hylinski
(74) *Attorney, Agent, or Firm* — James R. McDaniel

(57) ABSTRACT

An athletic speed and time measurement device, including a batter/runner, a baseball, a baseball bat, a plurality of baseball bases, wherein each of the plurality of baseball bases includes a batter/runner contact detection device, a baseball/baseball bat impact detecting device located on the baseball bat, or adjacent to (or attached to) the batter/runner, wherein the baseball/baseball bat impact detector detects an impact of the baseball with the baseball bat as the batter/runner swings the bat and contacts the baseball bat with the baseball, and a batter/runner timing device, wherein the batter/runner timing device determines an amount of time it takes for the batter/runner to run from a first of the plurality of baseball bases to a second of the plurality of baseball bases and displays the amount of time it takes for the batter/runner to run from a first of the plurality of baseball bases to a second of the plurality of baseball bases.

21 Claims, 10 Drawing Sheets

(56) References Cited

U.S. PATENT DOCUMENTS

| | | | |
|---|---|---|---|
| 4,998,727 A | 3/1991 | Person | |
| 5,868,578 A * | 2/1999 | Baum | A63B 24/0003 |
| | | | 434/247 |
| 6,042,492 A * | 3/2000 | Baum | A63B 24/0003 |
| | | | 434/257 |
| 6,661,342 B2 | 12/2003 | Hall et al. | |
| 8,477,046 B2 | 7/2013 | Alonso | |
| 8,821,305 B2 | 9/2014 | Cusey et al. | |
| 9,623,316 B2 | 4/2017 | Chapa, Jr. et al. | |
| 2007/0021242 A1* | 1/2007 | Krickler | A63B 24/0021 |
| | | | 473/451 |
| 2008/0032830 A1* | 2/2008 | Hooker | A63B 69/0002 |
| | | | 473/451 |
| 2008/0188353 A1* | 8/2008 | Vitolo | A61B 5/1036 |
| | | | 482/8 |
| 2009/0144785 A1* | 6/2009 | Walker | G11B 27/034 |
| | | | 725/105 |
| 2013/0014585 A1 | 1/2013 | Hetherington | |
| 2013/0346009 A1* | 12/2013 | Winter | G01S 13/58 |
| | | | 702/96 |
| 2014/0302950 A1* | 10/2014 | Burt | A63B 71/0622 |
| | | | 473/451 |

\* cited by examiner

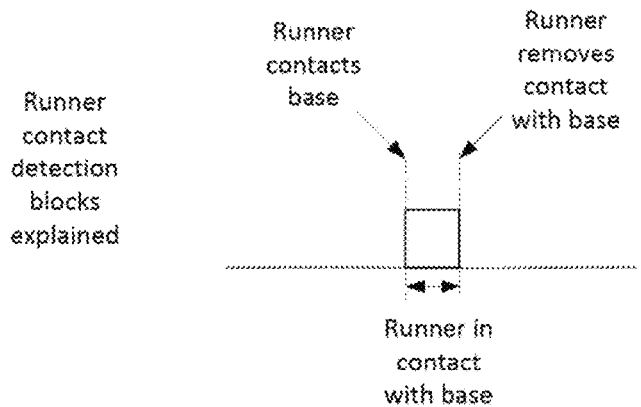
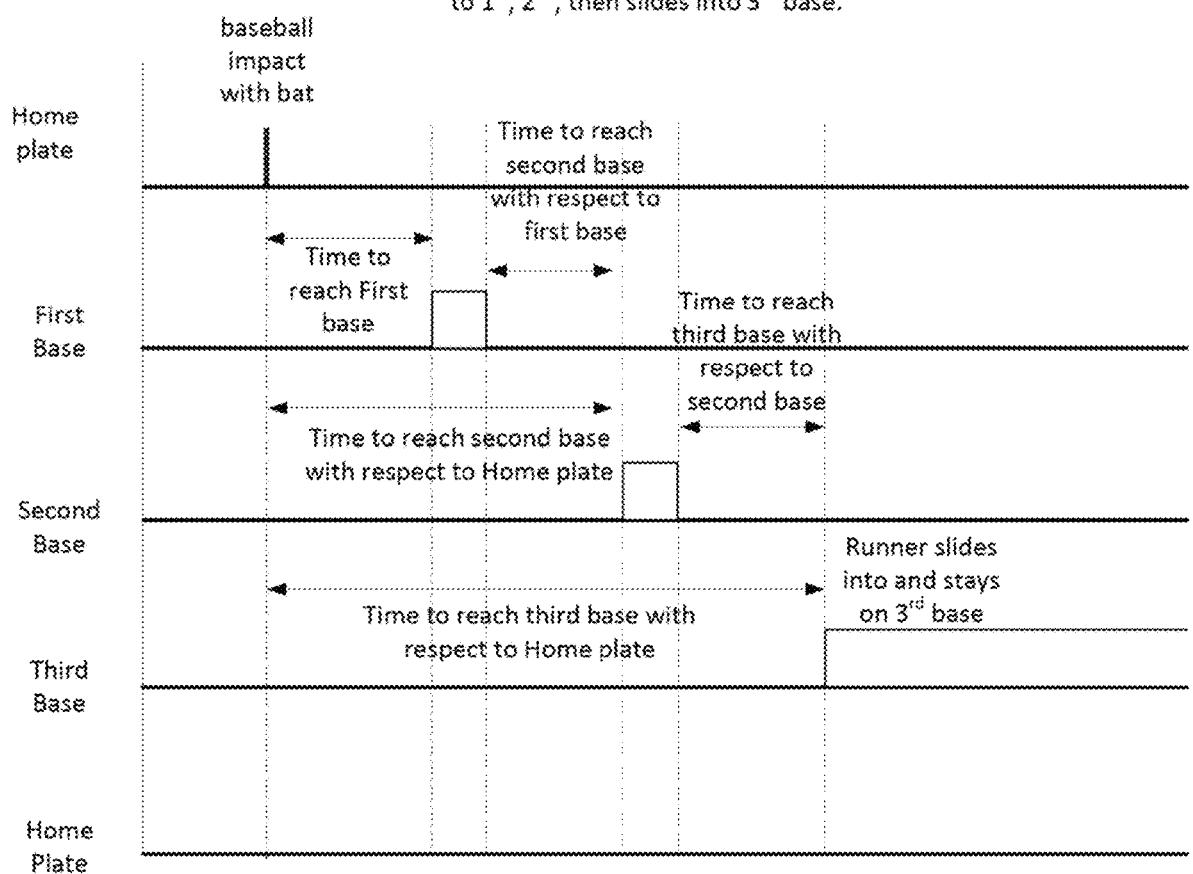
Figure 10

Example time reporting display for multirunner

Current Runners
Runner 1 = Tom
Runner 2 = Dick
Runner 3 = Harry

| | Tom | Dick | Harry | Best time Current Session | All time Field Best |
|---|---|---|---|---|---|
| Time from bat/ball contact to first base | 4.45 | 4.42 | 4.31 | Harry 4.31 | Harry 4.31 |
| Time from leaving batters box to first base | 4.35 | 4.33 | 4.25 | Harry 4.25 | Frank 4.2 |
| Batting to running transition time | 0.1 | 0.09 | 0.06 | Harry 0.06 | Sam 0.05 |
| Time from first to second base | 4.25 | 4.21 | 4.3 | Dick 4.21 | Ben 4.1 |
| Time from second to third base | 4.3 | 4.25 | 4.33 | Dick 4.25 | Miles 4.2 |
| Time from third to home base | 4.26 | 4.33 | 4.25 | Harry 4.25 | Joe 4.22 |

Figure 11A

Example time reporting display for individual runner

Base running summary for: Ben

| | Current time | Average | Min | Max | Field Best |
|---|---|---|---|---|---|
| Time from bat/ball contact to first base | 4.45 | 4.42 | 4.31 | 4.50 | Harry 4.31 |
| Time from leaving batters box to first base | 4.35 | 4.33 | 4.25 | 4.41 | Frank 4.2 |
| Batting to running transition time | 0.31 | 0.25 | 0.20 | 0.38 | Sam 0.10 |
| Time from first to second base | 4.33 | 4.15 | 4.10 | 4.42 | Ben 4.1 |
| Time from second to third base | 4.39 | 4.38 | 4.33 | 4.42 | Miles 4.2 |
| Time from third to home base | 4.26 | 4.33 | 4.25 | 4.36 | Joe 4.22 |

Figure 11B

ATHLETIC SPEED AND TIME MEASUREMENT DEVICE AND METHODS OF MAKING AND USING SAME

CROSS-REFERENCE TO RELATED APPLICATIONS

This application is a continuation-in-part of U.S. Provisional Patent Application Ser. No. 62/537,409, filed Jul. 26, 2017, the disclosure of which is hereby incorporated by reference in its entirety to provide continuity of disclosure to the extent such a disclosure is not inconsistent with the disclosure herein.

FIELD OF THE INVENTION

The present invention is generally related to an athletic speed and time measurement device. The speed and time measurement device precisely captures the exact instance when the batter/runner left the starting position as well as when and where he/she touched the target base. More particularly, the speed and time measurement device utilizes a sensor that would allow the timer to begin when the baseball is struck by the baseball bat and stop when the batter/runner reaches a particular base such as first base. Also, the speed and time measurement device can be used to determine the speed and time of the batter/runner when running between the bases. Finally, the speed and time measurement device also is able to keep a log of data (such as the player's speed and time) for each player to display for review or to download for further analysis to improve or monitor for changes in performance.

BACKGROUND OF THE INVENTION

Prior to the present invention, as set forth in general terms above and more specifically below, it is known, to employ various types of athletic speed and time measurement devices including stop watches. For example, a stopwatch or timing gates may be used to determine how fast a baseball player can run. The disadvantages of these systems are that they only evaluate how fast a player can run and do not take into account actions such as batting and touching a base. Consequently, a fast runner may have slow base running times if the proper technique is not used when transitioning from batting to running and proper base running techniques are not utilized. Some examples of base running considerations include running through and not stopping at first base, proper base rounding by touching the portion of the base that provides the runner with the fastest times around multiple bases, and time differences between bases when comparing sliding versus running or different sliding techniques such as foot first versus hand first.

It is further known, to employ various types of athletic speed and time measurement devices. See for example, U.S. Pat. No. 3,363,243 by Morley, U.S. Pat. No. 4,194,101 by Berseth, U.S. Pat. No. 4,627,620 by Yang, U.S. Pat. No. 4,998,727 by Person, U.S. Pat. No. 6,661,342 by Hall et al., U.S. Pat. No. 8,477,046 by Alonso, U.S. Pat. No. 8,821,305 by Cusey et al., U.S. Pat. No. 9,623,316 by Chapa, Jr. et al., U.S. Patent Application 2013/0014585 by Hetherington, U.S. Patent Application 2014/0302950 by Burt, and Chinese Patent 205608825. While these various athletic speed and time measurement devices may have been generally satisfactory, there is nevertheless a need for a new and improved athletic speed timer that precisely captures the exact instance when the batter/runner left the starting position and when he/she touched the target base and keeps track of data (such as the player's speed or the time it took to run between bases) for each player to show improvement or to show the effects of transitioning from batting to running or the time difference to reach a particular base for various slide techniques.

It is a purpose of this invention to fulfill these and other needs in the athletic speed and time measurement device art in a manner more apparent to the skilled artisan once given the following disclosure.

BRIEF SUMMARY OF THE INVENTION

A first aspect of the present invention is an athletic speed and time measurement device, including a batter/runner, a baseball, a baseball bat, a plurality of baseball bases, wherein each of the plurality of baseball bases includes a batter/runner contact detection device, a baseball/baseball bat impact detecting device located adjacent to the batter/runner, wherein the baseball/baseball bat impact detector detects an impact of the baseball with the baseball bat as the batter/runner swings the bat and contacts the baseball bat with the baseball, and a batter/runner timing device, wherein the batter/runner timing device determines an amount of time it takes for the batter/runner to run from a first of the plurality of baseball bases to a second of the plurality of baseball bases such that the amount of time it takes for the batter/runner to run from the first of the plurality of baseball bases to the second of the plurality of baseball bases is determined by a difference in time between when the baseball/baseball bat impact detector detects the impact of the baseball with the baseball bat, the batter/runner runs from the first of the plurality of baseball bases to a second of the plurality of baseball bases, and the contact detection device on the second of the plurality of baseball bases detects that the batter/runner has contacted the second of the plurality of baseball bases.

In one embodiment of the first aspect of the present invention, the batter/runner contact detection device further includes a vibration sensor operatively connected to each of the plurality of baseball bases.

In another embodiment of the first aspect of the present invention, the batter/runner contact detection device further includes a touch sensor operatively connected to each of the plurality of baseball bases.

In a further embodiment of the first aspect of the present invention, the baseball/baseball bat impact detecting device further includes at least one microphone operatively connected to the first of the plurality of baseball bases.

In yet another embodiment of the first aspect of the present invention, the baseball/baseball bat impact detecting device further includes at least one microphone located adjacent to the first of the plurality of baseball bases.

In still another embodiment of the first aspect of the present invention, the baseball/baseball bat impact detecting device further includes at least one baseball/baseball bat impact detector operatively attached to the batter/runner.

In an even further embodiment of the first aspect of the present invention, the baseball/baseball bat impact detecting device further includes a batting tee having a first end and a second end such that the first end of the batting tee is operatively connected to the first of the plurality of baseball bases, and a baseball/baseball bat impact detector operatively attached to the second end of the batting tee.

In another embodiment of the first aspect of the present invention, the batter/runner timing device further includes a mat located adjacent to the first of the plurality of baseball bases, wherein the batter/runner timing device determines an amount of time it takes for the batter/runner to run from the mat to the second of the plurality of baseball bases such that the amount of time it takes for the batter/runner to run from the mat to the second of the plurality of baseball bases is determined by a difference in time between when the baseball/baseball bat impact detector detects the impact of the baseball with the baseball bat, the batter/runner runs from the mat to the second of the plurality of baseball bases, and the contact detection device on the second of the plurality of baseball bases detects that the batter/runner has contacted the second of the plurality of baseball bases.

A second aspect of the present invention is an athletic speed and time measurement device for use during a sporting event, including a batter/runner, a baseball, a baseball bat, a plurality of baseball bases, wherein each of the plurality of baseball bases includes a batter/runner contact detection device, a baseball/baseball bat impact detecting device located adjacent to the batter/runner, wherein the baseball/baseball bat impact detector detects an impact of the baseball with the baseball bat as the batter/runner swings the bat and contacts the baseball bat with the baseball such that the baseball/baseball bat impact detecting device includes at least one microphone located adjacent to the first of the plurality of baseball bases, and a batter/runner timing device, wherein the batter/runner timing device determines an amount of time it takes for the batter/runner to run from a first of the plurality of baseball bases to a second of the plurality of baseball bases such that the amount of time it takes for the batter/runner to run from the first of the plurality of baseball bases to the second of the plurality of baseball bases is determined by a difference in time between when the baseball/baseball bat impact detector detects the impact of the baseball with the baseball bat, the batter/runner runs from the first of the plurality of baseball bases to a second of the plurality of baseball bases, and the contact detection device on the second of the plurality of baseball bases detects that the batter/runner has contacted the second of the plurality of baseball bases.

In another embodiment of the second aspect of the present invention, the batter/runner contact detection device further includes a vibration sensor operatively connected to each of the plurality of baseball bases.

In a further embodiment of the second aspect of the present invention, the batter/runner contact detection device further includes a touch sensor operatively connected to each of the plurality of baseball bases.

In yet another embodiment of the second aspect of the present invention, the baseball/baseball bat impact detecting device further includes at least one baseball/baseball bat impact detector operatively attached to the batter/runner.

In still another embodiment of the second aspect of the present invention, the baseball/baseball bat impact detecting device further includes a batting tee having a first end and a second end such that the first end of the batting tee is operatively connected to the first of the plurality of baseball bases, and a baseball/baseball bat impact detector operatively attached to the second end of the batting tee.

In a still further embodiment of the second aspect of the present invention, the batter/runner timing device further includes a mat located adjacent to the first of the plurality of baseball bases, wherein the batter/runner timing device determines an amount of time it takes for the batter/runner to run from the mat to the second of the plurality of baseball bases such that the amount of time it takes for the batter/runner to run from the mat to the second of the plurality of baseball bases is determined by a difference in time between when the baseball/baseball bat impact detector detects the impact of the baseball with the baseball bat, the batter/runner runs from the mat to the second of the plurality of baseball bases, and the contact detection device on the second of the plurality of baseball bases detects that the batter/runner has contacted the second of the plurality of baseball bases.

A third aspect of the present invention is a method for measuring an athletic speed and time, including the steps of providing a batter/runner, providing a baseball, providing a baseball bat, providing a plurality of baseball bases, wherein each of the plurality of baseball bases includes a batter/runner contact detection device, providing a baseball/baseball bat impact detecting device located adjacent or on the batter/runner, wherein the baseball/baseball bat impact detector detects an impact of the baseball with the baseball bat as the batter/runner swings the bat and contacts the baseball bat with the baseball, providing a batter/runner timing device, wherein the batter/runner timing device determines an amount of time it takes for the batter/runner to run from a first of the plurality of baseball bases to a second of the plurality of baseball bases such that the amount of time it takes for the batter/runner to run from the first of the plurality of baseball bases to the second of the plurality of baseball bases is determined by a difference in time between when the baseball/baseball bat impact detector detects the impact of the baseball with the baseball bat, the batter/runner runs from the first of the plurality of baseball bases to a second of the plurality of baseball bases, and the contact detection device on the second of the plurality of baseball bases detects that the batter/runner has contacted the second of the plurality of baseball bases, and determining a speed of the batter/runner based upon the amount of time it takes for the batter/runner to run from a first of the plurality of baseball bases to a second of the plurality of baseball bases.

In another embodiment of the third aspect of the present invention, the step of providing a batter/runner contact detection device further includes the step of providing a vibration sensor operatively connected to each of the plurality of baseball bases.

In yet another embodiment of the third aspect of the present invention, the step of providing a batter/runner contact detection device further includes the step of providing a touch sensor operatively connected to each of the plurality of baseball bases.

In a further embodiment of the third aspect of the present invention, the step of providing a baseball/baseball bat impact detecting device further includes the step of providing at least one microphone operatively connected to the first of the plurality of baseball bases.

In still another embodiment of the third aspect of the present invention, the step of providing a baseball/baseball bat impact detecting device further includes the step of providing at least one microphone located adjacent to the first of the plurality of baseball bases.

In a yet further embodiment of the third aspect of the present invention, the step of providing a baseball/baseball bat impact detecting device further includes the step of providing at least one baseball/baseball bat impact detector operatively attached to the batter/runner.

The preferred athletic speed and time measurement device, according to various embodiments of the present invention, offers the following advantages: ease of use; lightness in weight; durability; waterproof; dustproof; improved speed measurement characteristics; the ability to see the effect on the speed of a batter/runner when touching an object such as a base in the game of baseball; the ability to accurately measure the entire time period from when the baseball impacts the baseball bat to the time when the batter/runner touches the base(s); the ability to accurately measure the time between the moment the batter/runner's foot leaves one base and touches the next; the ability to report the batter/runner's foot or hand position on the base to provide data that could be used to reduce the running time; the ability to accurately detect the batter/runner's touch through the implementation of simple switch closures, vibration sensors, or other touch sensing technologies; the use of baseball base touch time and touch location data to aid with real game situations to show whether the fielder tagged the baseball base before the batter/runner or vice versa; the ability to measure the time to tag a base; and the ability to keep track of a player's improvement in speed. In fact, in many of the preferred embodiments, these advantages are optimized to an extent that is considerably higher than heretofore achieved in prior, known athletic speed and time measurement devices.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which:

FIG. 10 is an example of a timing diagram;

FIG. 11A is a schematic illustration of an example of a time reporting display for multiple runners; and FIG. 11B is a schematic illustration of an example of a time reporting display for an individual runner.

DETAILED DESCRIPTION OF THE PREFERRED EMBODIMENTS OF THE INVENTION

Figure 1:
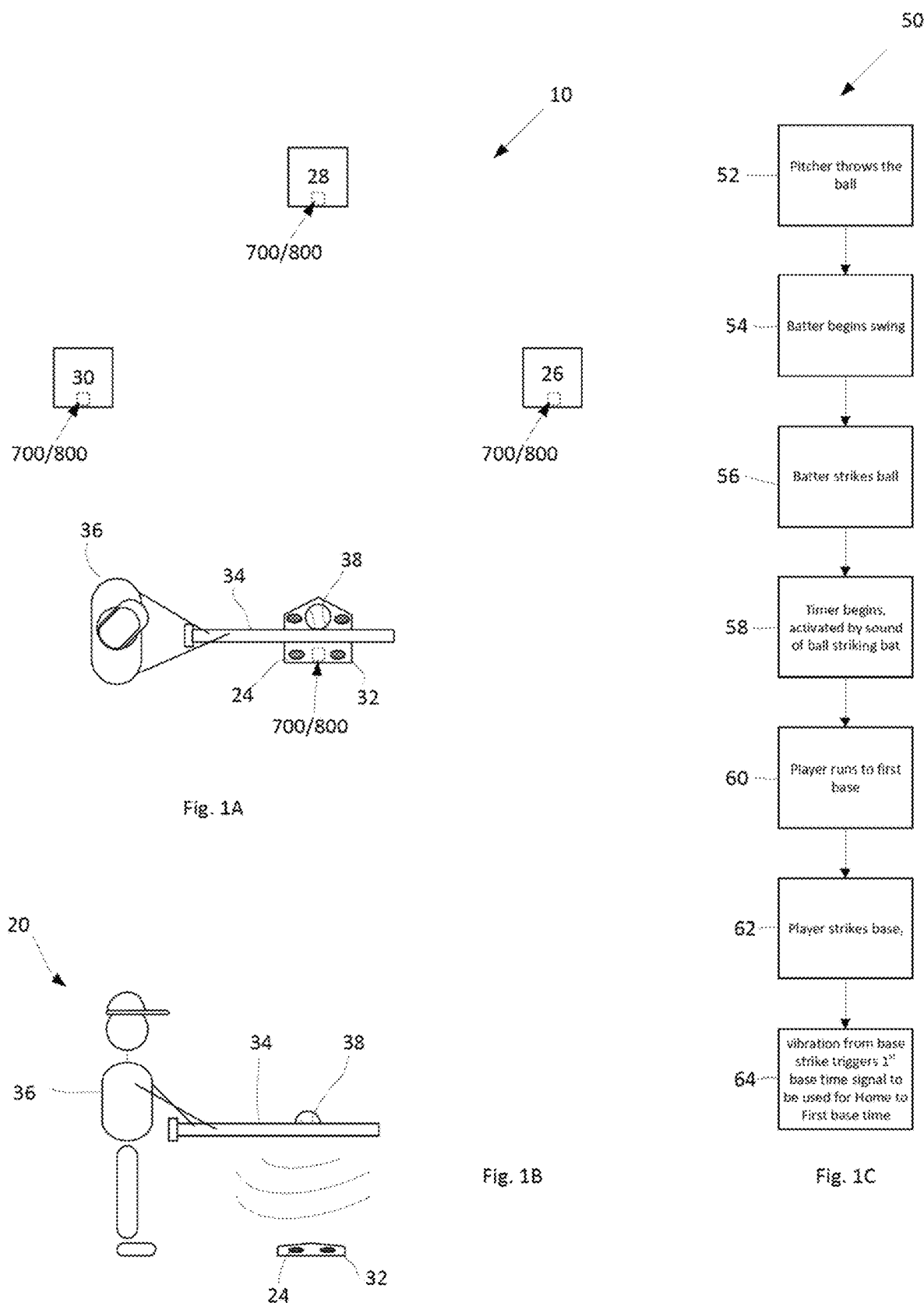
FIGS. 1A-1B are schematic illustrations of an athletic speed and time measurement device, according to one embodiment of the present invention.
FIG. 1C is a flowchart that illustrates the operation of embodiment of the present invention, as shown in FIGS. 1A and 1B.

Referring now to FIGS. 1A and 1B, there is illustrated athletic speed and time measurement device 10. As will be explained hereinafter in greater detail, the athletic speed and time measurement device 10 precisely captures the exact instance when the batter/runner left the starting position and when he/she touched the target baseball base. More particularly, the speed and time measurement device utilizes a sensor that would allow the timer to begin when the baseball is impacted by the bat and stop when the batter/runner reaches a particular baseball base such as first base. Also, the speed timer can be used to determine the speed and time of the batter/runner when running between the bases. Finally, the speed and time measurement device also is able to keep track of data (such as the player's speed and time) for each player to show improvement or changes in performance.

It is to be understood that with respect to the athletic speed and time measurement device 10, some batters have a very long follow through after hitting the baseball and even though they are very fast runners, their time to first base may be slower than a batter that quickly drops his/her bat and starts running. To understand the time added to reach first base by striking the ball, the batter can first time himself/herself using the athletic speed and time measurement device 10 with a base timing pad under the feet of the batter in the batter's box and the timing device in first base. The batter can then compare this time to the base timing system using the reported time from the baseball/bat impact detection to the base timing device in first base. The difference in these times is the time added by transitioning from batting to running. The user can make changes to their transition to running or evaluate how different their time to first is when bunting versus hitting since these different swings may result in different transition times from hitting to running. Alternatively, the batter/runner can determine their transition time by taking the difference in timing measurements produced from ball/bat strike detection and batter box departure detection (using either mat described or other occupancy detection technologies)

It is to be further understood that the athletic speed and time measurement device 10 can also be used to measure and optimize multi-base runs and allow precise timing measurements to evaluate the timing differences with various base touching locations or techniques as well as various slide techniques.

As shown in FIGS. 1A and 1B, athletic speed and time measurement device 10 includes, in part, athletic speed timer 20, microphones/vibration detectors 24, bases 26, 28, and 30, homeplate 32, conventional baseball bat 34, batter/runner 36 and conventional baseball 38.

With respect to athletic speed and time measurement device 20, in this embodiment, conventional microphones 24 are conventionally located in and/or on homeplate 32, top surface or edges in order to measure and/or record the sound of the baseball 38 striking the baseball bat 34, as will be described in greater detail later. In this manner, when the batter/runner 36 contacts the baseball 38 with the baseball bat 34, the sound of the impact of the baseball 38 upon the baseball bat 34 is conventionally detected by the microphone(s) 24 located in and/or on homeplate 32. It is to be understood that microphone refers to any transducer capable of converting sound into electrical energy. As will be discussed in greater detail later, this detection of the impact of the baseball 38 upon the baseball bat 34 is used to determine the speed and time of the batter/runner 36 in getting from homeplate 32 to a particular base such as first base 26.

It is to be understood that the sound from a baseball 38 striking a baseball bat 34 is distinct and is discernable from among the many other sounds at a baseball field. The frequency content may be analyzed and evaluated for distinct frequencies that are present for particular baseball bat compositions. Such content distinctions may include high sound levels and particular frequency spectrum, strong individual tones or multiple tones. Once this frequency content related to baseball bat 34/baseball 38 impacts is collected and analyzed, the start of a timer can be triggered on these particular sounds and other non-baseball bat 34/baseball 38 impact sounds could be ignored.

It is to be further understood that the processing of frequency content and sound levels associated with baseball bat 34/baseball 38 impacts may have some delays in processing of circuitry or software, along with the natural delay of sound travel and electronic or radio frequency (RF) communication which may need to be accounted for in the timing system depending on the desired level of reporting precision and accuracy. Fixed delays may be able to be accounted for with a calibration step in production or by the user, while variable processing delays may use a precision clock 710 (FIGS. 8 and 9) and circuitry or microcontroller to measure each timing event and compensate for any detection processing delays. The processing delays may be measured with the main microcontroller 712 (FIGS. 8 and 9), as well as with a separate auxiliary microcontroller or circuit (not shown) used solely for measuring processing delays.

For any delays that do not have a fixed duration and change with each timing event, a precision clock 710 may be used in the athletic speed and time measurement device 20 to allow the microcontroller 712 to initiate additional timer channels to time the total processing time to be added back into the batter's running time from home to first base. For example, a sound level detector conventionally located in the base may trigger the athletic speed and time measurement device 20 to begin the detection algorithm while additional timers may be initiated to measure the time it takes to perform processing on the sound content to verify if it was a valid event.

For example, different methods for baseball bat 34/baseball 38 impact detection can be, but are not limited to the following:

A. Sound level alone:
1. The athletic speed and time measurement device 20 may be triggered on the baseball bat 34/baseball 38 impact sound alone and rely on the batter touching first base to validate the event. Typically, the baseball bat 34/baseball 38 impact sound is a unique sound with a short duration that is discernable from other sounds in and around the batting area. If the batter did not strike first base and another loud sound occurs (possible baseball bat 34/baseball 38 impact) then the athletic speed and time measurement device 20 would initiate a new timer event and again wait for the batter to run and touch first base to validate the event. Home plate may also be implemented with touch and impact sensing capabilities to ensure that anyone striking the base (which may create measurable sound event) with either their foot, bat, or catcher's glove does not trigger an unintentional timing event. Any processing delays would be compensated for to allow reporting as accurate a time as possible.

B. Sound level with filter:
1. Athletic speed and time measurement device 20 may use a conventional filter (hardware or software) on the received signals from the microphone(s). The filter will pass only frequency content associated with a baseball 38 striking a baseball bat 34. The filter which is conventionally located at the base will allow immediate timer trigger start, based on acoustic level since the only acoustic levels that would reach the athletic speed and time measurement device 20 would be content associated with baseball bat 34/baseball 38 impacts. It is to be understood that the filter is conventionally located at the base so that the base only needs to report to the system a timing event. Any processing delays would be compensated for to allow reporting as accurate a time as possible.

C. Sound level followed by processing:
1. The start time of athletic speed and time measurement device 20 may be triggered and create a time stamp by the sound level of the baseball bat 34/baseball 38 impact then upon trigger, the athletic speed and time measurement device 20 would process the frequency content of the event to determine whether the sound was a baseball bat 34/baseball 38 impact. If processing confirms that it was a baseball bat 34/baseball 38 impact, then athletic speed and time measurement device 20 would use the time stamp from the initial sound level detection. Any processing delays would be compensated for to allow reporting as accurate a time as possible.

D. Frequency content triggered with processing time adjusted for:
1. The athletic speed and time measurement device 20 may trigger only on events that meet frequency content requirements indicative of a baseball bat 34/baseball 38 impact. In this instance, the processing time has been determined and is repeatable with a margin of error much smaller than needed for timing a runner between bases. Once it has been determined through processing that the athletic speed and time measurement device 20 detected a baseball bat 34/baseball 38 impact, the processing time will be subtracted.

Figure 5:
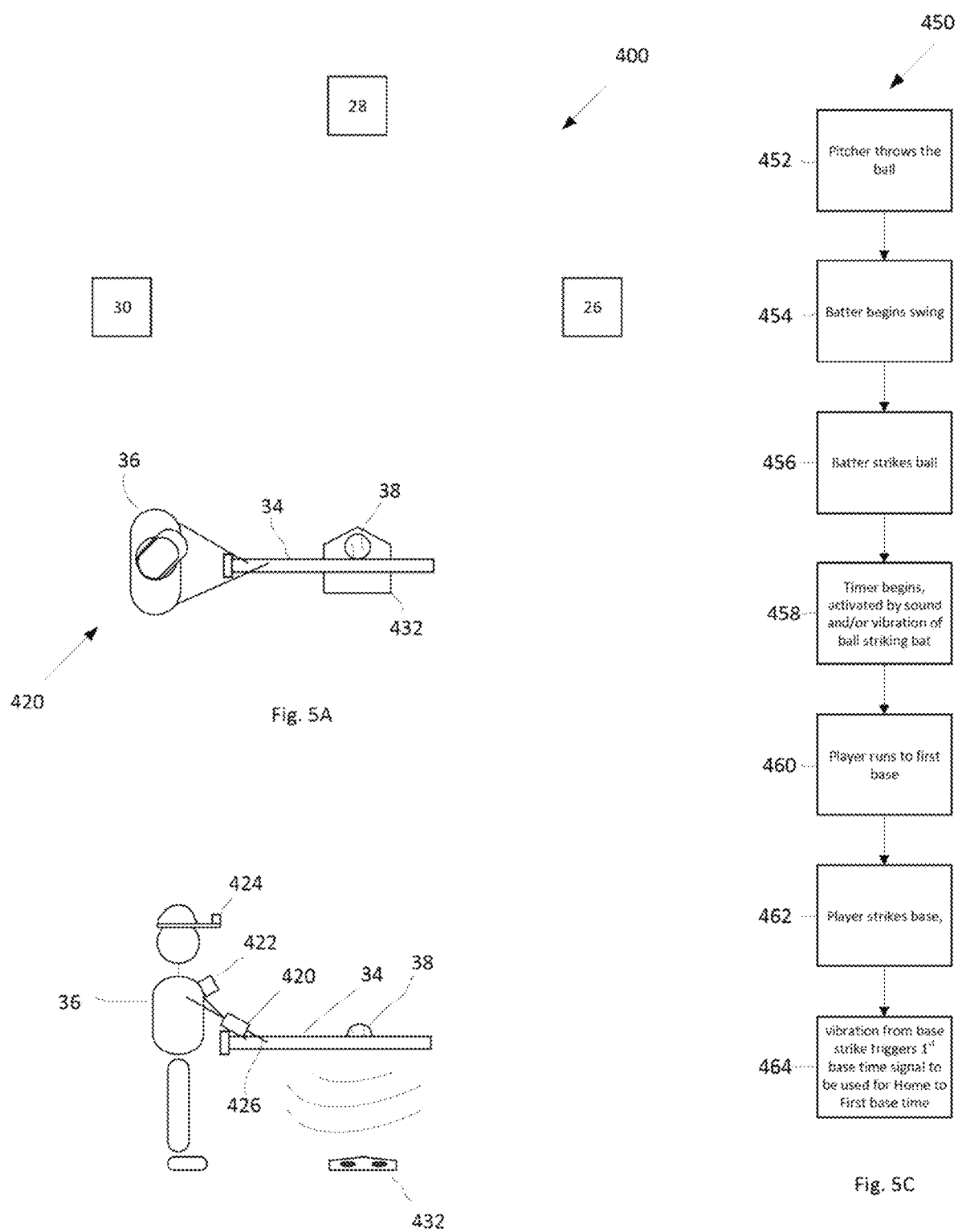
FIGS. 5A and 5B are schematic illustrations of an athletic speed and time measurement device, according to a fifth embodiment of the present invention.
FIG. 5C is a flowchart that illustrates the operation of embodiment of the present invention, as shown in FIGS. 5A and 5B.

E. Bat detection
1. Detection of a baseball bat 34/baseball 38 impact may be performed at the bat 34 by detecting a vibration or sound emitting from the baseball bat 34 upon a baseball bat 34/baseball 38 impact either with a conventional sensor attached to the baseball bat 34 or by a conventional wearable device (420, 422, and/or 424) attached to the batter (FIG. 5B).

It is to be understood that frequency spectrum analysis or filters can be used to compare measured results with baseball bat 34/baseball 38 impacts of differing bat technologies, including but not limited to, wood, composite, aluminum, steel. In this manner, the frequency spectrum analysis or filters can be used to look for a particularly strong frequency content in a particular part of the audio spectrum and or a particularly strong individual frequency.

Furthermore, frequency content from a baseball 38 being caught by a baseball glove is also characterized to allow the athletic speed and time measurement device 20 to ignore this event or alternatively the athletic speed and time measurement device 20 may be configured to utilize this sound for a newly configured timing measurement such as the time difference between when the catcher caught the ball and when any runner reached a base.

With respect to athletic speed and time measurement device 20, it is to be understood that different types of well-known electronic signal transmitting systems can be used in order to allow athletic speed and time measurement device 10 to assist in the determination of the speed of the batter/runner. For example, each base (26, 28, 30, 32) could be equipped with a unique communication identifier as well as touch/position sensor(s) 702 and/or vibration sensor(s) 704 (FIG. 8) to be used in a wireless communication system or touch/position sensor(s) 802 and/or vibration sensor(s) 804 (FIG. 9) to be used in a wired communication system. More particularly, each base (26, 28, 30, 32) could report an event (such as the contact of the foot of batter/runner 36 with that particular base) to a master device 714. In this manner, master device 714 conventionally calculates time and speed based on the reported base data received. It is to be understood that the master device 714 is equipped with a precise clock 710 and the bases (26, 28, 30 and 32) just need to report the time stamps or impact event caused by the batter/runner 36 to the master device 714. It is to be understood that precision clock may be used to synchronize all the time docks on all other base sensing devices such that any time reported from another base would be precise. This timeclock synchronization can occur at first power up, at the detection of first use, or at some regular interval.

It is also to be understood that the time stamp from any event (such as the contact of the foot batter/runner 36 with that particular base) should be universal and accessible to all baseball park equipment. It is to be understood that the phrase "universal" means that either the base running system generates the signal (precise time information) and the other ballpark equipment has access to it or the base running system receives a precise signal from existing ballpark equipment. In this manner, during video playback, it is possible to review the time that the baseball is caught by the baseball player covering that particular base and compare this time to the time reported by athletic speed timer system 10 that the batter/runner 36 touched the baseball base in order to determine if the batter/runner 36 is out. This unique aspect of the present invention more accurately determines if the batter/runner 36 reached base safely without the need to review multiple different video feeds.

It is to be understood that with respect to the baseball contact sensor technology to be implemented throughout many of the embodiments of the present invention, the baseball 38 contacting the baseball bat 34 starts the timer for the batter/runner 36. The detection of this event could be accomplished by using microphones 24 to conventionally detect the sound level and or the frequency content of the baseball bat 34/baseball 38 impact. Also, vibration caused by the baseball bat 34/baseball 38 impact could be detected in the baseball bat 34 or a device mechanically coupled closely enough to detect vibrations such as equipment that a batter may wear or baseball bat add on devices and trigger the timer from the large vibration generated by a baseball bat 34 impacting the baseball 38.

With respect to the microphone detection, conventional microphone circuitry can be used to detect the sound of the baseball 38 impacting the baseball bat 34 in multiple ways:
1. Sound level trigger—Fixed or adjustable sound level trigger(s) that would trigger off of a loud sound from the baseball bat 34 impacting the baseball 38 to start the timer.
2. Frequency content trigger—Microphone circuitry using signal processing to identify the specific frequency content created by baseball bat 34 impacting the baseball 38 and the ability to filter out unwanted frequencies such as crowd noise or the sound of the ball impacting the catcher's mitt.
3. Microphone array—Microphone array configuration to reduce noise and focus the gain at baseball bat 34/baseball 38 impact region.

It is to be understood that multiple microphones 24 (FIGS. 1A and 1B) may be used and arranged such that conventional beam forming can be used and focused at the batter/runner 36 to improve the signal level and minimize noise from other areas of the field or behind home plate 32.

Furthermore, batter location awareness using occupancy/vacancy detection technologies may also be used to assist the microphones 24 in locating the position of the batter 36 in order to optimize the sound of the baseball bat 34/baseball 38 impact reaching the microphone(s) 24. It is to be understood that location awareness can be used to focus microphone gain in the region near the batter as well as used alone to detect when the runner has left the batter's box.

It is to be further understood that the microphones 24 will need to be robust and be constructed so that they are waterproof and dustproof.

It is to be even further understood that a single microphone 24 may be used or an array of microphones 24 may be used and positioned so that beam forming would be enabled to allow the microphones 24 to focus their gain at the baseball bat 34/baseball 38 impact region above home plate and less gain from audience sounds or sounds from behind home plate, such as the catcher or umpire.

With respect to vibration detection, a vibration sensing device (not shown) could be attached or built into a baseball bat 34 to start a timer when the vibrations of a baseball 38 impacts baseball bat 34. It is to be understood that a vibration sensing device (not shown) could be attached or built into a baseball base (26, 28, 30) and/or home plate 32. For example, the vibration detection devices could include, but are not limited to the following:
1. Accelerometer,
2. Piezo sensor;
3. Electrical connection induced by vibration between spring and center metallic post; or
4. LED and photo sensor one of which is capable of moving with base vibration.

Regarding the baseball contact sensing implementation details, in order to detect the baseball 38 impacting the baseball bat 34, a vibration sensing or acoustic sensor (703, 704 or 802, 803, 809 in FIGS. 8 and 9) could be added as an auxiliary piece of equipment to the baseball bat 34 of the batter/runner 36, built into a new custom baseball bat 34, or, as a microphone system, built into the base (26, 28, 30, 32), nearby the batter/runner 36, or on the batter/runner 36 (such as a wearable device (420, 422, and/or 424 as shown in FIGS. 5A-5C). It is to be understood that an alternative approach could be to utilize a sensor (not shown) in a baseball 38 or built into a baseball tee (FIGS. 4A and 4B) that would sense the hitting of the baseball 38 but not impede the batter/runner 36 from passing through home plate 32 as they would normally do in a game situation.

It is to be further understood that another alternative to transfer baseball 38/baseball bat 34 impact data is to use a speaker (not shown) built into the baseball bat 34, baseball bat accessory, or wearable device wherein the speaker emits a tone when vibration is detected from the baseball 38 impacting baseball bat 34. This tone could then be detected by homeplate and used to trigger the start of the timer. This acoustic tone can either be audible or inaudible.

It is to be understood that another unique aspect of the present invention is the baseball bat 34/baseball 38 impact learning capabilities. In particular, the present invention employs microphone circuitry with learning abilities that allows the user to learn/improve the recognition of the baseball bat 34/baseball 38 impact frequency content since different baseball bat technologies have differing frequency content. The end user simply could enter a learn mode and have batting practice with the preferred baseball bat construction over the microphone system. The baseball bat 34/baseball 38 impact sensing algorithm (not shown) would then save this frequency content as a baseball bat 34 to baseball 38 impact which would help improve the timer start capabilities. Preprogrammed baseball bat types with the ability to detect typical frequency content from common bat designs could be included to provide immediate functionality.

Still another unique aspect of the present invention is the ability of athletic speed and time measurement device 10 to calculate the speed of the batter/runner 36. In particular, athletic speed and time measurement device 10 provides for the calculation of speed of the batter/runner 36 in mph (or kilometers/hour) or feet per second (or meters/second) by having the end user enter the distance between baseball bases (26, 28, 30 and 32) or having the ability to automatically measure the distance between bases (26, 28, 30 and 32) using conventional range finding capabilities.

Also, athletic speed and time measurement device 10 is used to calculate base run time from two possible main events. In the case of practice base running, the timer would be started when the foot of the batter/runner 36 left the starting mat 220 (FIGS. 3A and 3B) or any of the possible bases. In the case of a game situation, the timer may be configured to start when the baseball 38 impacted the baseball bat 34 and the impact is detected. The time to first base 26 would be determined from the base running system data as shown in FIG. 10 and as follows (It is to be understood that time stamp refers to complete timing information communicated in the system which would allow base timing calculations):

> Homeplate 32 to first base 26 time(game situation)=1base impact time stamp–Ball impact time stamp.

> Homeplate 32 to first base 26(practice situation)=1$^{st}$ base impact time stamp–starting mat time stamp Time between any other bases would be calculated by taking the difference between base time stamps. For example, the time from first base 26 to second base 28=2$^{nd}$ base impact time stamp–1$^{st}$ base impact time stamp.

In the instance of a non-universal clock configuration or non-master device 714 system, every base in the system would keep the previous base impact event (that was received through the communication means, such as RF or wired) saved and would report the time between the previous and current base strikes, at a given base. For example, when the runner impacts first base, a base strike from first base is communicated to other bases, second base receives this communication and starts a timer to determine the runners time to second base. Second base would then report the time locally or to a main system display the time it took the runner to run from first to second base.

Multi base speed timing—the base runner could practice full speed with the requirement to touch multiple bases. This mode would allow reporting of average speed between bases along with time data. It is to be understood that for between base running, the detection of the runner's foot leaving the base may be preferred in timing calculations over the initial impact since there will be a slight difference in time between the foot striking the base and leaving the base. As such, both leaving the base and impact times may be reported for analysis.

It is to be understood that a batter/runner 36 touching or striking a base 26, 28, 30 and/or 32 can be detected by all or combinations of impact, sound, vibration, or touch caused by a batter/runner 36. The sound created by the batter/runner touching the base may be detected using one or more microphones. The process of touching the base 26, 28, 30 and/or 32 with any part of the body of batter/runner 36 causes pressure on the base that should be able to be sensed with various conventional sensor technologies. Not only does the batter/runner 36 impose pressure on the base 26, 28, 30 and/or 32 when a particular base is touched by the batter/runner 36 but also an impact event with vibrations is created when the batter/runner 36 touches the base. This impact and vibration can also be used for detection that a base has been touched. The detection of the batter/runner 36 touching the base may be accomplished with a conventional accelerometer conventionally located within the base.

It is to be further understood that the accelerometer can be conventionally configured to detect a base strike by the batter/runner 36. In this manner, the base strike may show up as a ringing waveform and the detection may be any change in signal, a signal above a threshold, or a particular waveform type or frequency of ringing. Furthermore, the accelerometer may utilize the differences of impact waveforms or detection levels to distinguish between a batter/runner 36 and a defensive player (not shown).

In particular, a separate triggering mechanism conventionally located in the base may be used that detects impact or touch separate from determining impact direction or impact force. In this manner, impact, touch location, and accelerometer X, Y and Z data can be stored (in memory 703/803) on a conventional, continuous fixed interval storage loop with the understanding that the storage loop is long enough to ensure not overwriting base running data. In this embodiment, the trigger circuit is designed to be very responsive to touch or impact in order to aid in precise timing capture and to avoid false triggers associated with very low detection threshold levels Furthermore, the recorded accelerometer data is evaluated, reviewing impact location, force, and direction of impact to confirm the impact event was caused by a runner and not a defensive player. An example of this separate trigger circuit or mechanism and data logging in parallel is as follows. Runner tags base, the large force triggers the very responsive trigger circuit, but the runners time is slightly earlier than the trigger circuit detected since the runners touch on the bag shows up as a quickly increasing signal. To obtain the precise time of first impact, the system may use the time obtained from the trigger circuit or system and review the signals earlier time measurements (with respect to the large signal level) down to the smaller signal level (very first instant of touch on base without full body force imparted on base) to obtain a more precise time when the runner first touched the bases.

It is to be understood that in embodiments that use an accelerometer, it would be best for the athletic speed and time measurement device 10 to know the X, Y and Z axes with relation to the baseball field to aid in determination of the batter/runner 36 advancing around the bases verses a fielder tagging a base (since x vs y forces on accelerometer would appear differently when force is applied from different directions upon the base). The base (or the device added to the base) can be marked in such a way that the end user could install them in a consistent fashion with labels for each base indicating the direction of installation. Alternatively, the athletic speed and time measurement device 10 can learn the orientation of installation from earlier trigger events. For example, the end user installs all the bases and then another batter/runner 36 runs around all of the bases and touches all of the bases so that the athletic speed and time measurement device 10 will be able to evaluate the accelerometer and or touch location data to determine the orientation of each base with respect to the baseball diamond in order to allow for later determination between a batter/runner 36 and a fielder touching any given base.

It is to be further understood that it is important to be able to distinguish between types of impacts using various sensors. For example, a fielder's impact on a base may be different from a runner's in the location of touch on the base, the force with which the base is touched as well as the duration of the touch on any given base. A runner's touch or impact is likely to be on the portion of the base that provides the greatest speed in advancing to another base as well as higher impact and shorter duration. In some situations, the fielder and base runner may both strike or impact the bag simultaneously or almost simultaneously in given play. In this instance, the location of the strike or touch on the base may be used to assist in determination as to whether the batter/runner 36 is out or safe for a given play as well as allowing timing data to be determined when multiple impact or touch events occur.

Furthermore, the accelerometer may be configured in continuous impact detection mode to instantly indicate when a base touch event has occurred. The impact threshold may be set by default, adjustable, or learned from use. Also, there may be signals on all axes measurements and the athletic speed and time measurement device 10 can be set to the highest sensitivity and priority to the direction the runner would be impacting the base. Conversely, the sensitivity of the athletic speed and time measurement device 10 can be reduced to detect base strikes that would be associated with a fielder from the opposing team covering a base in order to try to get a batter/runner 36 out.

It is to be further understood that the base may be equipped with touch sensitive capabilities so that the location of the touch can be detected. The touch location is useful in that it can be used to distinguish whether the touch was from a batter/runner 36 that is advancing around the bases or the opposing team trying to get a batter/runner 36 out. For example, a batter/runner 36 running from home plate to first is likely to tag first base at the location closest in distance from home plate. Detecting a touch at this location would likely need a time stamp to be used in the timing system, as opposed to a tag or sustained contact on the base closest in distance to the pitcher's mound. The athletic speed and time measurement device 10 would be able to detect the runner's foot print on the base since a batter/runner 36 rounding the bases would be touching the base there.

It is to be understood that there may be a delay between the time the batter/runner 36 impacts or touches the base compared to the time of first detection by circuitry. This delay may be characterized and compensated for to provide higher levels of precision and accuracy. In particular, by utilizing a conventional, predictable natural ringing frequency from a batter/runner's departure from a base, athletic speed and time measurement device 10 should be able to calculate the beginning of the departure of the runner from a base for an accurate timing capture. Alternatively, once a triggerable event has occurred, the athletic speed and time measurement device 10 can review previous signals in time until steady state levels are detected to use the first detected change in signal level after steady state as the start time.

With respect to the detection of a foul ball, a pop up or a fly out, when the impact between the baseball bat 34 and the baseball results in a tipped ball, a foul ball, a pop up or a fly out, the athletic speed and time measurement device 10 includes an automatic reset. For example, if a tipped ball, a foul ball, a pop up or a fly out is hit by the batter/runner 36, typically, the batter/runner 36 simply remains at homeplate 32 or runs down to first base 26 at a reduced speed. In this instance, if after a predetermined period of time, for example, 10 seconds, has passed and the batter/runner 36 has not contacted or otherwise interacted with first base 26, athletic speed and time measurement device 10 will automatically reset (if configured to utilize this feature). It is to be understood that athletic speed and time measurement device 10 resets or starts the timing operation again upon detection of a baseball/baseball bat impact or when a new batter/runner 36 steps upon homeplate 32 (after some programmed time period to avoid a reset since the runner may strike homeplate while running to first base 26). In a practice mode, the athletic speed and time measurement device 10 resets or starts the timing operation again if the batter/runner 36 touches any base out of order such as when the batter/runner 36 wants to practice sliding into second base 28 from the starting position of first base 26.

It is to be further understood that a yet another unique aspect of the present invention is that athletic speed and time measurement device 10 can be configured (if desired) to account for stride length of the batter/runner 36. In this manner, the difference in stride length between a taller/older batter/runner 36 and a shorter/younger batter/runner 36 can be accounted for by athletic speed and time measurement device 10. This will allow for competition from all levels and still provide a competitive game, by adjusting times to be equivalent to the same stride length thereby creating an even challenge between participants both tall and short.

Another unique aspect of the present invention is the use of a display device in order to display the base running information of the batter/runner 36. For example, information related to the speed of the batter/runner 36, the time it took for the batter/runner to go from homeplate 32 to a particular base (including homeplate 32), and the time it took for the batter/runner 36 to go between particular bases (including homeplate 32) could be displayed. An example of this display readout can be found in FIGS. 11A and 11B.

In particular, as shown in FIG. 11A, various information related to multiple runners can be conventionally displayed. For example, the time from bat/ball contact to first base, the time from leaving the batter's box to first base, the batting to running transition time, the time from first to second base, the time from second to third base, the time from third base to home plate can be displayed for multiple runners. Also, similar information for an individual runner can be displayed, as shown in FIG. 11B. It is to be understood that other information related to the multiple runners/individual runner can be displayed.

It is to be understood that the base running information can be displayed in a number of different locations. The base running information could be displayed in any or all of the following locations:

1. Score board;
2. On any or all bases so that batter/runner 36 could look at the side of the base after it is reached to see their time;
3. Smartphone or mobile device of batter/runner 36 or spectator,
4. Wearable device located on the batter/runner 36, such as a watch, necklace or heads up display;
5. Dedicated base runner system display; and/or
6. Built into any or all of the base running timing equipment or master device.

Figure 8:
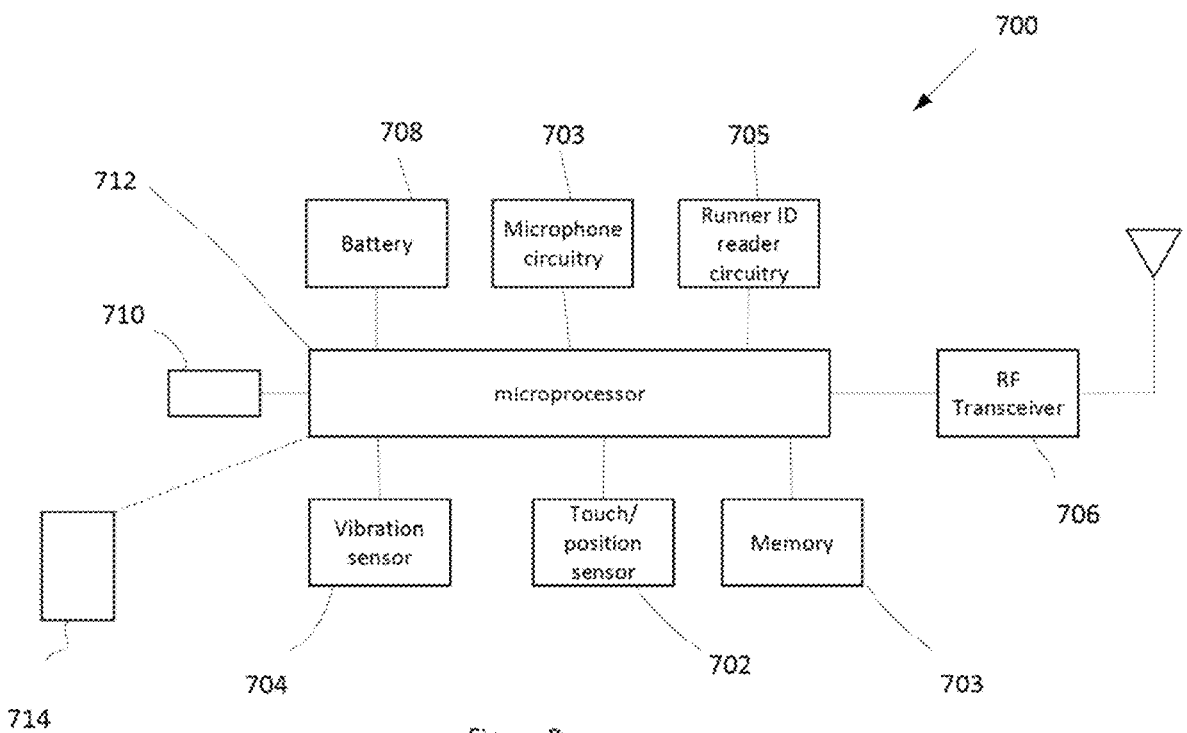
FIG. 8 is a block diagram of a wireless radio-frequency (RF) communication baseball base module, according to the present invention.
Figure 9:
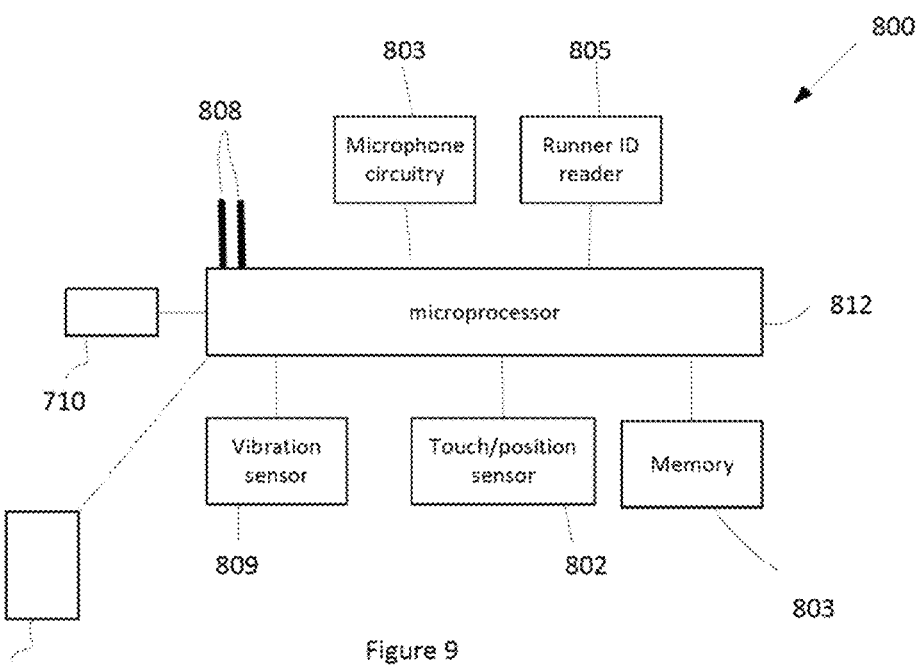
FIG. 9 is a block diagram of a wired communication baseball base module, according to the present invention.

It is to be further understood that the bases (26, 28, 30 and 32) would have the ability to store multiple time stamps within a close time duration to assist in helping to determine whether the batter/runner is out or safe in defensive plays, as discussed previously. Furthermore, the time data of the batter/runner 36 during practice sessions could include more comprehensive statistics including an average, minimum, and maximum for each base segment, as previously discussed. Athletic speed and time measurement device 10 could include an RFID tag reader, a barcode scanner, or any other identifying technology to capture and store individual results and recall them during subsequent training sessions to evaluate whether their base running times have improved. For example, each base may contain an RFID tag reader (705/805) that registers the runner's identification while they are in the process of base running so that their particular base running times can be captured and stored. It is to be understood that wireless module 700 and wired module 800 is to include RFID tag reader (705/805), as shown in FIGS. 8 and 9. For simplicity, only wireless module 700 and wired module 800 are depicted in FIG. 1A. However, it is to be understood that wireless module 700 and wired module 800 (including RFID tag reader (705/805) along with vibration sensor 704/809 and touch/position sensor 7021802) can also be located on the bases in FIGS. 2A, 3A, 4A, 5A, 6 and 7. Furthermore, it is to be understood that RFID tag reader (705/805), vibration sensor 704/809 and touch/position sensor 702/802) can be located on top of the base, within the base, under the base and adjacent to the base. It should be noted that the RFID tag reading may occur before the runner has actually struck the base unlike vibration sensors 704 or 809 which will capture the actual base strike time. Another implementation includes runner identification reading at one location (either at a particular base, any base, or as a new device in the system) before a runner starts using the system and all subsequent times will be captured and stored with that runner's identification until a new identification is entered. When the runner identification feature is utilized, the runner identification information will be included in any base timing events being communicated/transmitted to any devices in the system in either the wired or wireless configuration. In this way, all base running data can be stored and compiled for each runner individually at the master device 714 or any individual device. There may also be an option for manual entry of the runner's identification into the system.

During the operation of athletic speed and time measurement device 10, reference is made to FIGS. 1A-1C. In particular, as shown in FIG. 1C, method 50 for operating athletic speed and time measurement device 10 is illustrated. As shown in FIG. 1C, the method 50 begins with the pitcher throwing the baseball 38 (step 52).

After the pitcher throws the baseball 38, the batter/runner 36 waits for the baseball 38 to approach homeplate 32. As the baseball 38 approaches homeplate 32, the batter/runner 36 makes a determination as to whether or not the batter/runner 36 is going to swing at the pitch. If the batter/runner 36 likes the pitch, the batter/runner will swing at the pitch (step 54).

If the batter/runner 36 has properly swung the baseball bat 34, the baseball bat 34 should contact the thrown baseball 38 such that the baseball bat 34 impacts the thrown baseball 38 (step 56).

As shown in step 58, the impact of the baseball 38 with the baseball bat 34 creates an audible sound that is detected by microphones/vibration detectors 24. This detection by microphones/vibration detectors 24 is forwarded to master device 714. At this point, the master device 714 begins the timing of the speed of the batter/runner 36 (step 58).

Assuming that the impact between the baseball 38 and the baseball bat 34 did not result in a tipped ball, a foul ball, a pop up or a fly out, the batter/runner 36 drops the baseball bat 34 and begins running towards first base 36 (step 60).

While the batter/runner 36 is running towards first base 26, master device 714 is continuing to keep track of the time between when the impact of the baseball 38 and baseball bat 34 was detected and when the batter/runner 36 contacts or otherwise interacts with first base 26 (step 62).

As shown in step 64, once the batter/runner 36 has contacted or otherwise interacted with first base 26, the impact or vibration caused by the batter/runner 36 contacting first base 26 is detected by first base 26, as will be discussed in greater detail later. Once the impact or vibration of the batter/runner 36 upon first base 26 is detected, this information is electronically sent to the master device 714. The master device 714 then conventionally calculates the speed of the batter/runner 36, as previously discussed.

Finally, various information related to the speed of the batter/runner 36 and/or the time it took for the batter/runner 36 to reach a particular base can then be displayed, as previously discussed. At this point, athletic speed and time measurement device 10 automatically resets for the next batter/runner 36 from a timeout or a new batter/runner 36 touches homeplate 32. However, it is to be understood that athletic speed and time measurement device 10 also can be used to keep track of a batter/runner 36 that has made it safely onto base. In this manner, athletic speed and time measurement device 10 can be used to keep track of the speed, time or other information related to this batter/runner 36 in order to calculate the speed, time or other information of the batter/runner 36 as he/she progresses around the other bases (28, 30 and 32).

Figure 2:
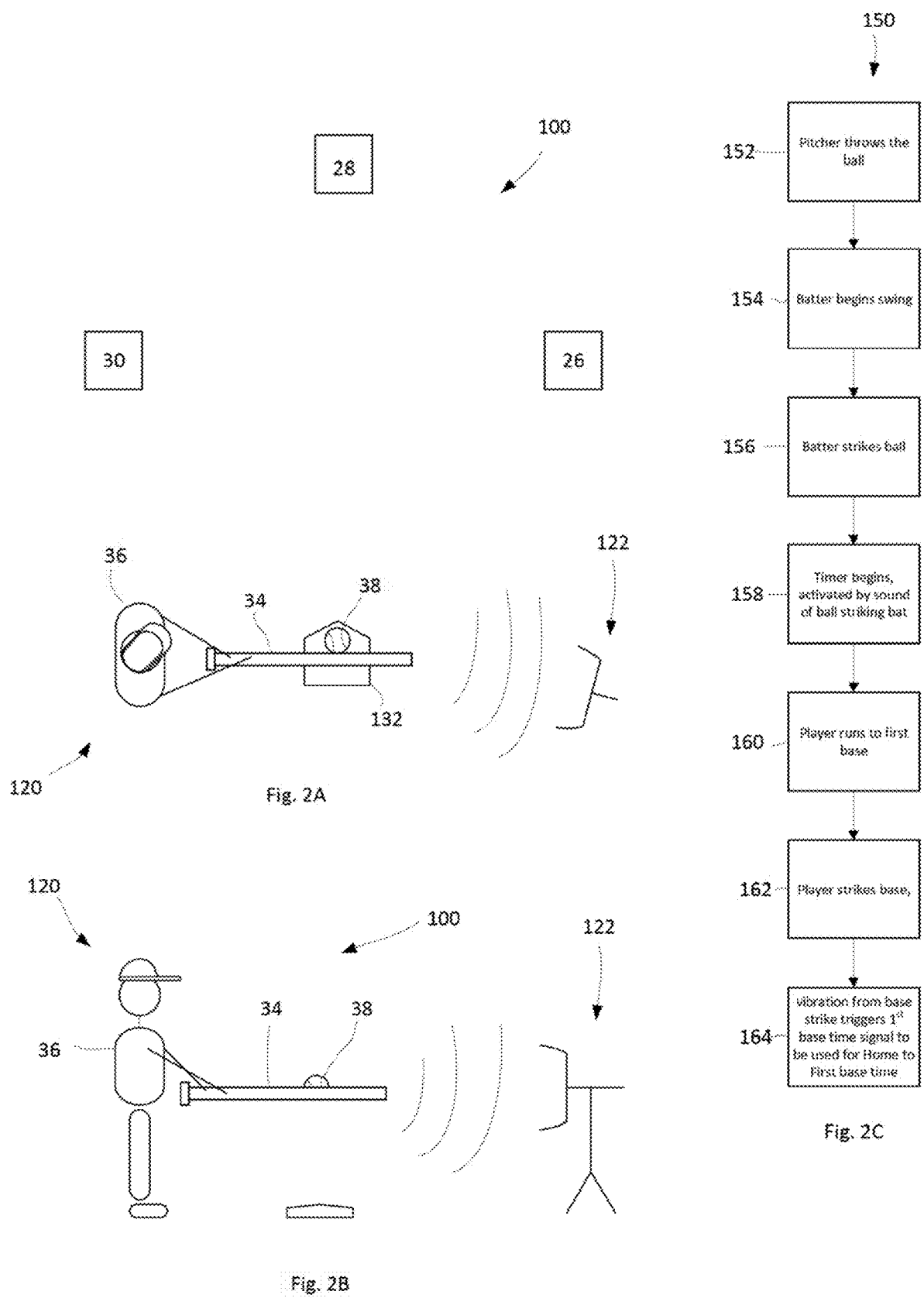
FIGS. 2A and 2B are schematic illustrations of an athletic speed and time measurement device, according to a second embodiment of the present invention.
FIG. 2C is a flowchart that illustrates the operation of embodiment of the present invention, as shown in FIGS. 2A and 2B.

With respect to FIGS. 2A-2C, there is illustrated another embodiment of the present invention. In this embodiment, in athletic speed and time measurement device 100 the timer in master device 714 is started by the sound created by the baseball 38 impacting the baseball bat 34. Microphones 122 located near home plate 132 process the sound of the baseball 38 impacting the baseball bat 34 and start the timer in master device 714 if a baseball 38/baseball bat 34 impact event is detected.

Regarding athletic speed and time measurement device 100, it is to be understood that athletic speed and time measurement device 100 is constructed with many of the same components as athletic speed and time measurement device 10 such as baseball bases 26, 28, 30, homeplate 132, baseball bat 34, batter/runner 36 and baseball 38. The major difference between athletic speed and time measurement device 100 and athletic speed and time measurement device 10 being the location and use of microphone 122. It is to be further understood that athletic speed and time measurement device 100 is used in substantially the same manner as athletic speed and time measurement device 10, as will be discussed in greater detail later.

With respect to microphone 122, preferably, microphone 122 is any suitable, durable microphone that is capable of detecting the impact between baseball 38 and baseball bat 34. Also, it is to be understood that microphone 122 should be located at a distance from homeplate 132 so as to be able to adequately detect the impact between baseball 38 and baseball bat 34 and electronically transmit the detection of the impact between baseball 38 and baseball bat 34 to master device 714.

During the operation of athletic speed and time measurement device 100, reference is made to FIGS. 2A-2C. In particular, as shown in FIG. 2C, method 150 for operating athletic speed and time measurement device 100 is illustrated. As shown in FIG. 2C, the method 150 begins with the pitcher throwing the baseball 38 (step 152).

After the pitcher throws the baseball 38, the batter/runner 36 waits for the baseball 38 to approach homeplate 132. As the baseball 38 approaches homeplate 132, the batter/runner 36 makes a determination as to whether or not the batter/runner 36 is going to swing at the pitch. If the batter/runner 36 likes the pitch, the batter/runner will swing at the pitch (step 154).

If the batter/runner 36 has properly swung the baseball bat 34, the baseball bat 34 should contact the thrown baseball 38 such that the baseball bat 34 impacts the thrown baseball 38 (step 156).

As shown in step 158, the impact of the baseball 38 with the baseball bat 34 creates an audible sound that is detected by microphone 122. This detection by microphone 122 is forwarded to master device 714. At this point, the master device 714 begins the timing of the speed of the batter/runner 36 (step 158).

Assuming that the impact between the baseball 38 and the baseball bat 34 did not result in a tipped ball, a foul ball, a pop up or a fly out, the batter/runner 36 drops the baseball bat 34 and begins running towards first base 26 (step 160).

While the batter/runner 36 is running towards first base 26, master device 714 is continuing to keep track of the time between when the impact of the baseball 38 and baseball bat 34 was detected and when the batter/runner 36 contacts or otherwise interacts with first base 26 (step 162).

As shown in step 164, once the batter/runner 36 has contacted or otherwise interacted with first base 26, the impact or vibration caused by the batter/runner 36 contacting first base 26 is detected by first base 26, as will be discussed in greater detail later. Once the impact or vibration of the batter/runner 36 upon first base 26 is detected, this information is electronically sent to the master device 714. The master device 714 then conventionally calculates the speed of the batter/runner 36, as previously discussed.

Finally, various information related to the speed of the batter/runner 36 and/or the time it took for the batter/runner 36 to reach a particular base can then be displayed, as previously discussed. At this point, athletic speed and time measurement device 100 automatically resets for the next batter/runner 36. However, it is to be understood that athletic speed and time measurement device 100 also can be used to keep track of a batter/runner 36 that has made it safely onto base. In this manner, athletic speed and time measurement device 100 can be used to keep track of the speed, time, or other information related to this batter/runner 36 in order to calculate the speed, time, or other information of the batter/runner 36 as he/she progresses from one base to another base (28, 30 and 132).

Figure 3:
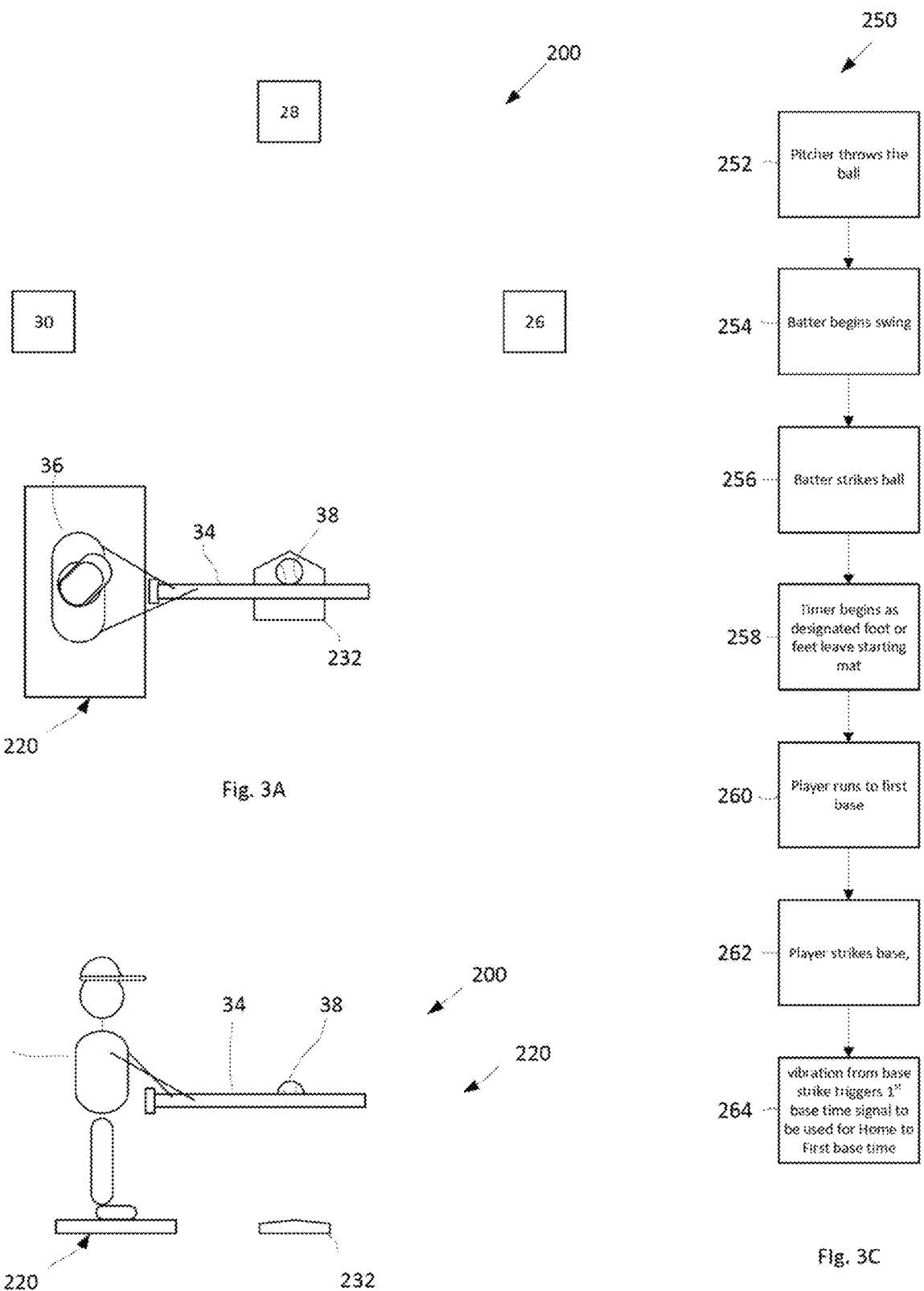
FIGS. 3A and 3B are schematic illustrations of an athletic speed and time measurement device, according to a third embodiment of the present invention.
FIG. 3C is a flowchart that illustrates the operation of embodiment of the present invention, as shown in FIGS. 3A and 3B.

With respect to FIGS. 3A-3C, there is illustrated a third embodiment of the present invention. In this embodiment, in athletic speed and time measurement device 200 the timer in master device 714 is started by one or both of the feet of the batter/runner 36 being lifted off of a mat 220 or by using one of the bases 26, 28, and/or 30. In this manner, athletic speed and time measurement device 200 would be used from base to base times as well as practice runs from home plate 232.

Regarding athletic speed and time measurement device 200, it is to be understood that athletic speed and time measurement device 200 is constructed with many of the same components as athletic speed and time measurement device 10 such as bases 26, 28, 30, homeplate 232, baseball bat 34, batter/runner 36 and baseball 38. The major difference between athletic speed and time measurement device 200 and athletic speed and time measurement device 10 being the location and use of mat 220. It is to be further understood that athletic speed and time measurement device 200 is used in substantially the same manner as athletic speed and time measurement device 10, as will be discussed in greater detail later.

With respect to mat 220, preferably, mat 220 is constructed of any suitable, durable material. Also, mat 220 includes conventional sensors that are capable of detecting when the batter/runner 36 has left homeplate 232. It is to be understood that the sensors can also be located adjacent to homeplate 232. In this manner, mat 220 is able to detect when one or both of the feet of batter/runner 36 have been lifted off of mat 220 and electronically transmit the detection of the removal of one or both of the feet of batter/runner 36 from mat 220 to master device 714.

During the operation of athletic speed timer system 200, reference is made to FIGS. 3A-3C. In particular, as shown in FIG. 3C, method 250 for operating athletic speed and time measurement device 200 is illustrated. As shown in FIG. 3C, the method 250 begins with the pitcher throwing the baseball 38 (step 252).

After the pitcher throws the baseball 38, the batter/runner 36 waits for the baseball 38 to approach homeplate 32. As the baseball 38 approaches homeplate 32, the batter/runner 36 makes a determination as to whether or not the batter/runner 36 is going to swing at the pitch. If the batter/runner 36 likes the pitch, the batter/runner will swing at the pitch (step 254).

If the batter/runner 36 has properly swung the baseball bat 34, the baseball bat 34 should contact the thrown baseball 38 such that the baseball bat 34 impacts thrown baseball 38 (step 256).

As shown in step 258, the detection of the removal of one or both of the feet of batter/runner 36 from mat 220 is forwarded to master device 714. At this point, the master device 714 begins the timing of the speed of the batter/runner 36 (step 258).

Assuming that the impact between the baseball 38 and the baseball bat 34 did not result in a tipped ball, a foul ball, a pop up or a fly out, the batter/runner 36 drops the baseball bat 34 and begins running towards first base 36 (step 260).

While the batter/runner 36 is running towards first base 26, master device 714 is continuing to keep track of the time between the detection of the removal of one or both of the feet of batter/runner 36 from mat 220 and when the batter/runner 36 contacts or otherwise interacts with first base 26 (step 262).

As shown in step 264, once the batter/runner 36 has contacted or otherwise interacted with first base 26, the impact or vibration caused by the batter/runner 36 contacting first base 26 is detected by first base 26, as will be discussed in greater detail later. Once the impact or vibration of the batter/runner 36 upon first base 26 is detected, this information is electronically sent to the master device 714. The master device 714 then conventionally calculates the speed and time of the batter/runner 36, as previously discussed.

Finally, various information related to the speed of the batter/runner 36 and/or the time it took for the batter/runner 36 to reach a particular base can then be displayed, as previously discussed. At this point, athletic speed and time measurement device 200 automatically resets for the next batter/runner 36. However, it is to be understood that athletic speed and time measurement device 200 also can be used to keep track of a batter/runner 36 that has made it safely onto base. In this manner, athletic speed and time measurement device 200 can be used to keep track of the speed and time or other information related to this batter/runner 36 in order to calculate the speed, time, or other information of the batter/runner 36 as he/she goes from one base to another base (28, 30 and 232).

Figure 4:
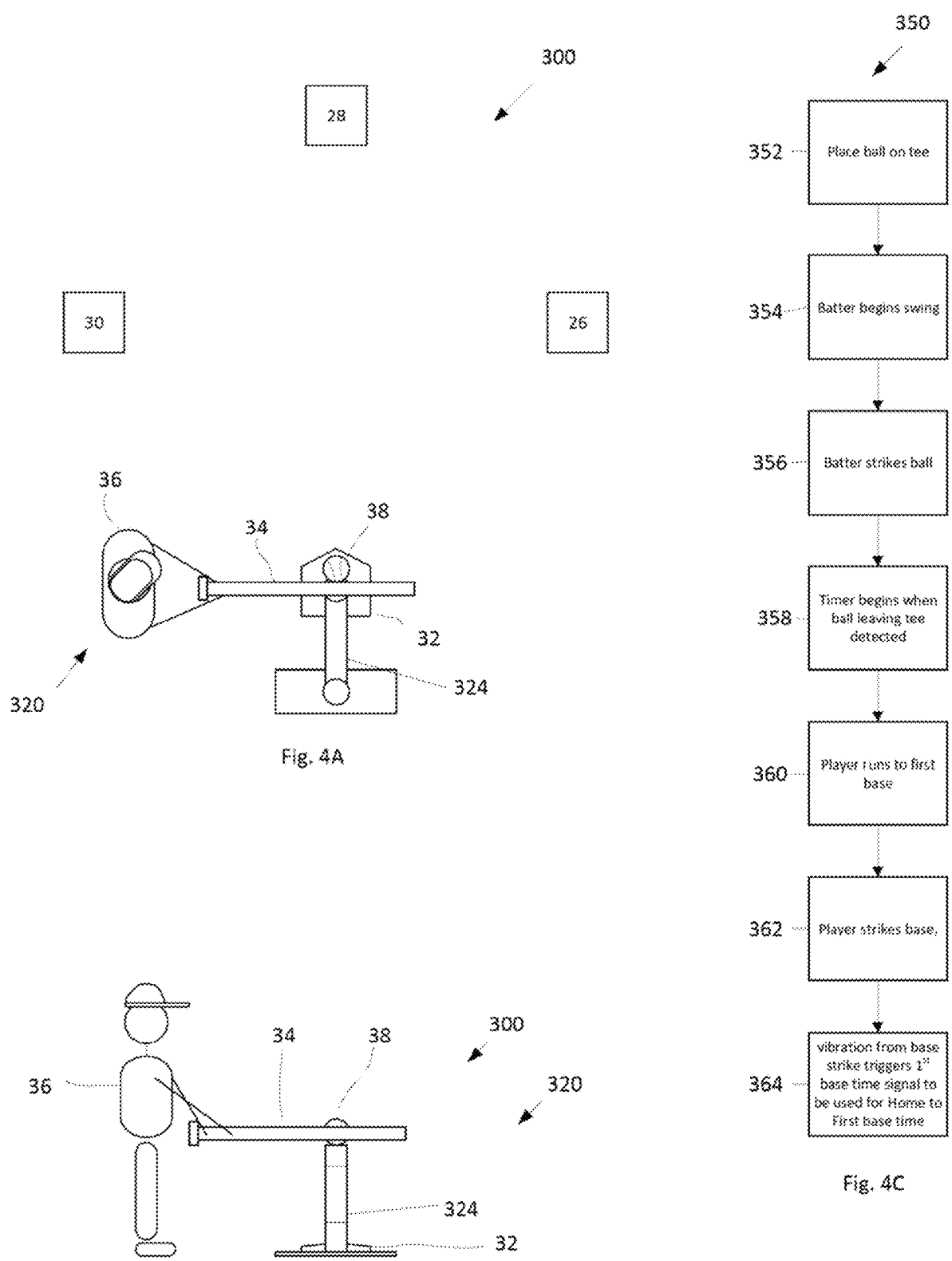
FIGS. 4A and 4B are schematic illustrations of an athletic speed and time measurement device, according to a fourth embodiment of the present invention.
FIG. 4C is a flowchart that illustrates the operation of embodiment of the present invention, as shown in FIGS. 4A and 4B.

With respect to FIGS. 4A-4C, there is illustrated a fourth embodiment of the present invention. In this embodiment, in athletic speed and time measurement device 300 the timer in master device 714 is started by a baseball 38 ball leaving a batting tee 324 which is conventionally attached to homeplate 32. It is to be understood that batting tee 324 may be located adjacent to homeplate 32. In this manner, batting tee 324 includes a conventional device to hold the baseball 38 over homeplate 32 and is able to swivel or otherwise move out of the way of homeplate 32 so as to not interfere with any batter/runner 36 who is trying to run to first base 26.

Regarding athletic speed and time measurement device 300, it is to be understood that athletic speed and time measurement device 300 is constructed with many of the same components as athletic speed and time measurement device 10 such as baseball bases 26, 28, 30, homeplate 32, baseball bat 34, batter/runner 36 and baseball 38. The major difference between athletic speed and time measurement device 300 and athletic speed and time measurement device 10 being the location and use of batting tee 324. It is to be further understood that athletic speed and time measurement device 300 is used in substantially the same manner as athletic speed and time measurement device 10, as will be discussed in greater detail later.

With respect to batting tee 324, preferably, batting tee 324 is constructed of any suitable, durable material. Also, batting tee 324 includes conventional sensors that are capable of detecting when the batter/runner 36 has impacted baseball 38 with baseball bat 34 so as to cause baseball 38 to leave the top of batting tee 324. In this manner, batting tee 324 is able to detect when batter/runner 36 has impacted baseball 38 with baseball bat 34 so as to cause baseball 38 to leave the top of batting tee 324 and electronically transmit the detection of baseball 38 leaving the top of batting tee 324 to master device 714.

During the operation of athletic speed timer system 300, reference is made to FIGS. 4A-4C. In particular, as shown in FIG. 4C, method 350 for operating athletic speed and time measurement device 300 is illustrated. As shown in FIG. 4C, the method 350 begins with the baseball 38 being placed on the top of batting tee 324, as is well known in the art of batting tees (step 352).

After the baseball 38 has been placed on the top of batting tee 324, the batter/runner 36 will swing at the baseball 38 (step 354).

If the batter/runner 36 has properly swung the baseball bat 34, the baseball bat 34 should contact the baseball 38 such that the baseball bat 34 impacts baseball 38 (step 356).

As shown in step 358, the detection of the removal of baseball 38 from the top of batting tee 324 is forwarded to master device 714. At this point, the master device 714 begins the timing of the speed of the batter/runner 36 (step 358).

Assuming that the impact between the baseball 38 and the baseball bat 34 did not result in a foul ball, a pop up or a fly out, the batter/runner 36 drops the baseball bat 34 and begins running towards first base 26 (step 360).

While the batter/runner 36 is running towards first base 26, master device 714 is continuing to keep track of the time between the removal of baseball 38 from the top of batting tee 324 and when the batter/runner 36 contacts or otherwise interacts with first base 26 (step 362).

As shown in step 364, once the batter/runner 36 has contacted or otherwise interacted with first base 26, the impact or vibration caused by the batter/runner 36 contacting first base 26 is detected by first base 26, as will be discussed in greater detail later. Once the impact or vibration of the batter/runner 36 upon first base 26 is detected, this information is electronically sent to the master device 714. The master device 714 then conventionally calculates the speed and time of the batter/runner 36, as previously discussed.

Finally, various information related to the speed of the batter/runner 36 and/or the time it took for the batter/runner 36 to reach a particular base can then be displayed, as previously discussed. At this point, athletic speed and time measurement device 300 automatically resets for the next batter/runner 36. However, it is to be understood that athletic speed and time measurement device 300 also can be used to keep track of a batter/runner 36 that has made it safely onto base. In this manner, athletic speed and time measurement device 300 can be used to keep track of the speed, time, or other information related to this batter/runner 36 in order to calculate the speed and time or other information of the batter/runner 36 as he/she progresses around the other bases (28, 30 and 32).

With respect to FIGS. 5A-5C, there is illustrated a fifth embodiment of the present invention. In this embodiment, in athletic speed and time measurement device 400 the timer in master device 714 is started by a wearable device (420, 422, and/or 424) on the batter/runner 36 which detects the sound and/or vibration created by the baseball 38 impacting the baseball bat 34. It is to be understood that a wearable device can also be located in a batting glove 426 that is being worn by the batter/runner 36.

Regarding athletic speed and time measurement device 400, it is to be understood that athletic speed and time measurement device 400 is constructed with many of the same components as athletic speed timer system 10 such as baseball bases 26, 28, 30, homeplate 432, baseball bat 34, batter/runner 36 and baseball 38. The major difference between athletic speed and time measurement device 400 and athletic speed and time measurement device 10 being the location and use of wearable device (420, 422, and/or 424) on the batter/runner 36. It is to be further understood that athletic speed and time measurement device 400 is used in substantially the same manner as athletic speed and time measurement device 10, as will be discussed in greater detail later.

With respect to wearable device (420, 422, and/or 424), preferably, wearable devices (420, 422, and/or 424) are any suitable, durable wearable device that is capable of detecting the impact between baseball 38 and baseball bat 34. Also, it is to be understood that wearable device (420, 422, and/or 424) should be located on or near (in the case of acoustic devices, they may be worn by catcher or umpire) the batter/runner 36 so as to be able to adequately detect the impact between baseball 38 and baseball bat 34 and electronically transmit the detection of the impact between baseball 38 and baseball bat 34 to master device 714. For example, wearable device (420, 422, and/or 424) can be, but is not limited to, a wristband 420, a batting glove 426, a necklace 422, or a device 424 that is capable of being conventionally attached to the hat of the batter/runner 36.

During the operation of athletic speed and time measurement device 400, reference is made to FIGS. 5A-5C. In particular, as shown in FIG. 5C, method 450 for operating athletic speed and time measurement device 400 is illustrated. As shown in FIG. 5C, the method 450 begins with the pitcher throwing the baseball 38 (step 452).

After the pitcher throws the baseball 38, the batter/runner 36 waits for the baseball 38 to approach homeplate 32. As the baseball 38 approaches homeplate 32, the batter/runner 36 makes a determination as to whether or not the batter/runner 36 is going to swing at the pitch. If the batter/runner 36 likes the pitch, the batter/runner will swing at the pitch (step 454).

If the batter/runner 36 has property swung the baseball bat 34, the baseball bat 34 should contact the thrown baseball 38 such that the baseball bat 34 impacts the thrown baseball 38 (step 456).

As shown in step 458, the impact of the baseball 38 with the baseball bat 34 creates an audible sound or vibration that is detected by wearable device(s) (420, 422, 424, and/or 426). This detection by wearable device(s) (420, 422, 424, and/or 426) is forwarded to master device 714. At this point, the master device 714 begins the timing of the speed of the batter/runner 36 (step 458).

Assuming that the impact between the baseball 38 and the baseball bat 34 did not result in a tipped ball, a foul ball, a pop up or a fly out, the batter/runner 36 drops the baseball bat 34 and begins running towards first base 36 (step 460).

While the batter/runner 36 is running towards first base 26, master device 714 is continuing to keep track of the time between when the impact between the baseball 38 and baseball bat 34 was detected and when the batter/runner 36 contacts or otherwise interacts with first base 26 (step 462).

As shown in step 464, once the batter/runner 36 has contacted or otherwise interacted with first base 26, the impact or vibration caused by the batter/runner 36 contacting first base 26 is detected by first base 26, as will be discussed in greater detail later. Once the impact or vibration of the batter/runner 36 upon first base 26 is detected, this information is electronically sent to the master device 714. The master device 714 then conventionally calculates the speed and time of the batter/runner 36, as previously discussed.

Finally, various information related to the speed of the batter/runner 36 and/or the time it took for the batter/runner 36 to reach a particular base can then be displayed, as previously discussed. At this point, athletic speed and time measurement device 400 automatically resets for the next batter/runner 36. However, it is to be understood that athletic speed and time measurement device 400 also can be used to keep track of a batter/runner 36 that has made it safely onto base. In this manner, athletic speed and time measurement device 400 can be used to keep track of the speed and time or other information related to this batter/runner 36 in order to calculate the speed, time, or other information of the batter/runner 36 as he/she progresses around the other bases (28, 30 and 432).

Figure 6:
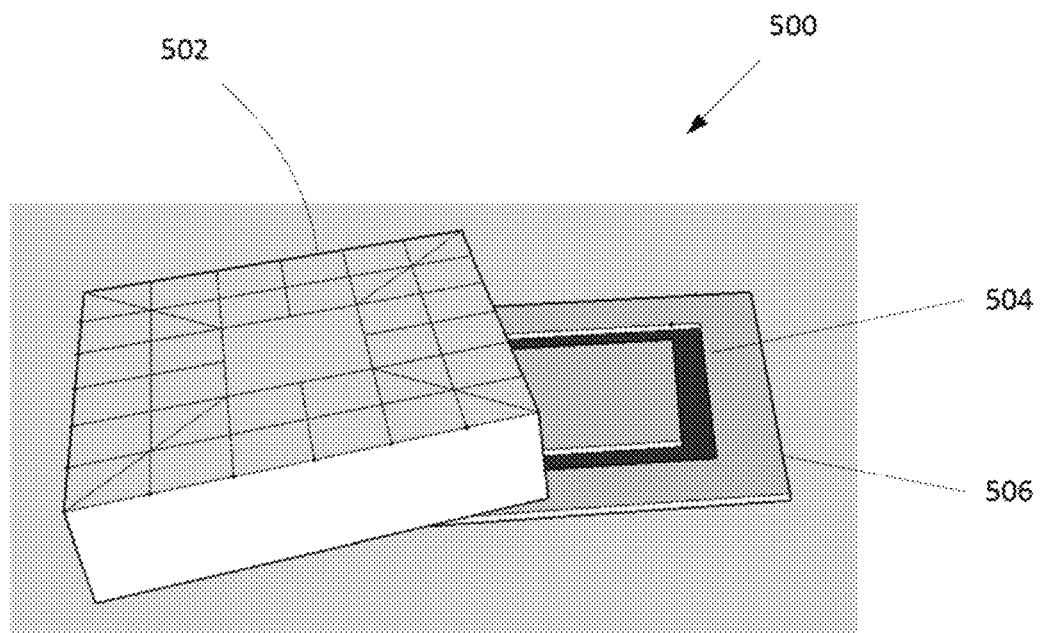
FIG. 6 is a schematic illustration of a baseball base modified according to one embodiment of the present invention.

With respect to FIG. 6, there is illustrated an embodiment of the baseball base module 500. It is to be understood that baseball bases 26, 28, 30, and 32 be modified, retrofitted or newly constructed with baseball base module 500 which includes any or all of the circuit components listed in either FIG. 8 or 9. In this manner, baseball base module 500 can be used to determine when the batter/runner 36 has contacted or otherwise interacted with a particular base in order to assist in the determination of the speed or time of the batter/runner 36.

Regarding baseball base module 500, baseball base module 500 is used for the speed and timing system and can be constructed into different variations. Possible implementation options include the following. 1. Replacement top cover 502 with timing module built in. 2. Replacement bottom base mounting plate 506 with built in timing module. 3. Retrofit insert 504 that is located between top plate 502 and the bottom base mounting plate 506. 4. New base cover that installs over top of existing top cover 502 containing timing module. It is to be understood that base timing module or base module refers to devices pictured in FIGS. 8 and 9. It is to be further understood that multiple individual touch and or vibration sensors can be built into any of the previous mentioned implementations in order to achieve sufficient vibration detection and impact position/location and or direction information. Additionally, base timing module or base module refers to devices pictured in FIGS. 8 and 9

Figure 7:
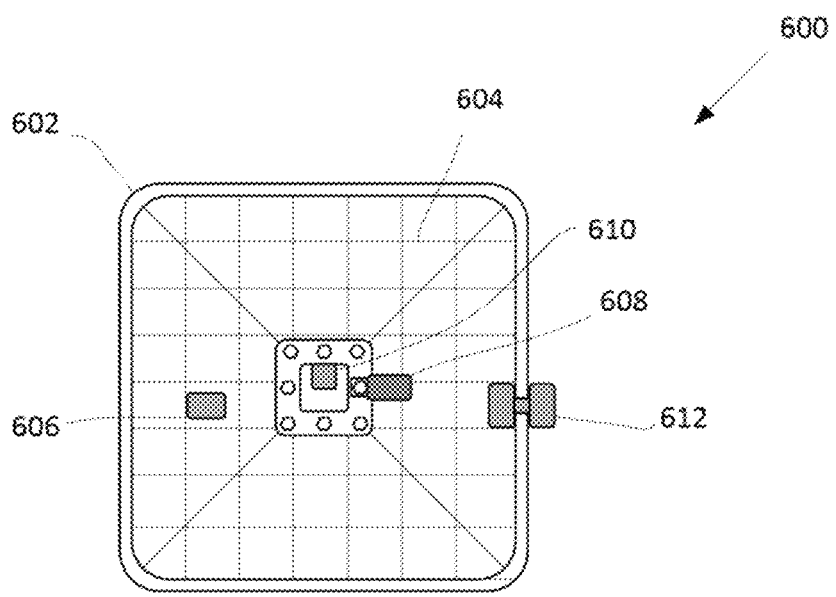
FIG. 7 is a schematic illustration of a baseball base modified according to a second embodiment of the present invention.

With respect to FIG. 7, there is illustrated an embodiment of the baseball base module 600. It is to be understood that baseball bases 26, 28, 30 and 32 can be modified with baseball base module 600 which includes any or all of the circuit components listed in either FIG. 8 or 9. In this manner, baseball base module 600 can be used to determine when the batter/runner 36 has contacted or otherwise interacted with a particular base in order to assist in the determination of the speed or time of batter/runner 36.

Regarding baseball base module 600, baseball base module 600 can be constructed into different variations. As shown in FIG. 7, a post module 610 can be conventionally attached to the inside of the post of base 602. Also, a webbing-based module 606 can be conventionally attached to the webbing 604 of base 602 and the underside of base 602. A bolt module 608 can be conventionally attached to the bolt (not shown) on base 602. Finally, the module 612 can be conventionally attached to the edge of the base. It is to be understood that multiple individual touch and or vibration sensors can be connected to a single module, multiple individual modules interconnected, or combinations of all listed implementations or locations can be used in order to achieve sufficient vibration detection and impact position/location and or direction information. Additionally, base timing module or base module refers to devices pictured in FIGS. 8 and 9. It is to be further understood that modules 606, 608, 610 and 612 may be used to house the RFID reader, the vibration sensor and/or the touch position sensor.

With respect to the baseball base modules 500 and 600, as discussed above, baseball base modules 500 and 600 are used to detect when the foot (or other body parts) of the batter/runner 36 contacts or otherwise interacts with the baseball base and the baseball base modules 500 and 600. It is to be understood that possible sensing technologies used to detect runner interactions with baseball bases included in baseball base modules 500 and 600 could be, but are not limited to, the following:

1. Conductive fabric within foam;
2. Pressure sensitive material such as Velostat®;
3. Vibration sensing devices such as mechanical, Piezo, Accelerometer;
4. Light blocking within the base by mechanical means;
5. Metal mesh separated with a separating material that allows connections when pressure is applied for impact detection and location of impact;
6. Capacitive sense on the top surface of the baseball base for detecting the batter/runner's impact location and triggering the timer;
7. Electrical switch contact closure to detect batter/runner striking the baseball base. Implemented with a two-piece base system where metal contacts would electrically connect when pressure is applied to the base;
8. Acoustic detection through the use of microphone(s) within the baseball base to listen for the loud sound of a batter/runner impacting the base; and
9. Light emitting diode (LED) on a non-fixed assembly installed in the baseball base. When the base is struck, a LED mechanically vibrates which alters the received light measurement by the receiving photo sensor indicating a batter/runner's impact upon the base.

It is to be further understood that mat 220 (FIGS. 3A and 3B) could also be constructed with baseball base modules 500 and 600.

It is to be further understood that baseball base modules 500 and 600 could be either added to the already existing baseball base in the form of a base cover or be a completely separate device in the same form factor as a baseball base or as a similar design with slightly different dimensions to allow for the ability to detect the batter/runner's position on a larger or smaller surface area. Alternatively, the baseball base modules 500 and 600 could be a small attachment to an existing base that keeps close physical contact to recognize the vibration created by the batter/runner's tag. Furthermore, baseball base modules 500 and 600 could also be a retrofit piece to an existing baseball base structure such as a top rubber pad that is normally designed to separate from the base mount for safety purposes. Additionally, the base module may be fitted inside the mounting base located in the ground. Finally, baseball base modules 500 and 600 could also be implemented between the bottom base and the top "break away" piece of the base system.

Another unique aspect of the present invention is that baseball base modules 500 and 600 could learn the optimal trigger point as it is used with different sized batters/runners 36. The user could put the baseball base modules 500 and 600 into a learn mode and the baseball base modules 500 and 600 would monitor the first few times the runner impacts the base and determine the proper detection threshold for the size of the batters/runners 36 using the athletic speed and time measurement devices 10, 100, 200, 300 and/or 400. The baseball base modules 500 and 600 could also learn the installed location by the location that the batters/runners 36 routinely strike the base or the direction of the majority of impacts.

In order to be able to electronically transmit when the batter/runner 36 contacts or otherwise interacts with a base 26, 28, 30 and/or 32, baseball base modules 500 and 600 can transmit the signal either through a wireless connection and/or a wired connection. The information communicated through either the wireless or wired link may include any or all of the following: Generic base impact notification, base impact notification with precise time stamp information, base location identification, runner identification, location of impact on base, base contact loss from the runner removing contact, periodic or continuous notifications of sustained contact if runner remains on base, and precision clock alignment signals (heartbeat) to calibrate all devices to the same time.

Regarding the wireless connection, as shown in FIG. 8, wireless modules 700 would be located in each baseball base along with wireless communication abilities to report base impact data to any other bases or modules to calculate a runner's time between bases. As shown in FIG. 8, wireless module 700, includes, in part, conventional touch/position sensor 702, conventional vibration sensor 704, a conventional radio frequency (RF) transceiver 706, a conventional battery 708, a conventional precision clock 710, a conventional microphone system 703, a conventional runner ID system (such as RFID) 705, and conventional microprocessor 712.

As can be seen in FIG. 8, touch/position sensor 702 and vibration sensor 704 are connected to microprocessor 712.

As is well known in the wireless communications art, once the batter/runner 36 contacts or otherwise interacts with a base, the touch/position sensor 702 and/or vibration sensor 704 is activated and the signal is conventionally transmitted to the microprocessor 712. The microprocessor 712 is then used to transmit, through the use of the RF transceiver 706, to master device 714 the timing data of the batter/runner 36 so that the speed and time of the batter/runner 36 can be calculated by the master device 714, as discussed above. Finally, the speed and time of the batter/runner 36 is then transmitted to the display device (not shown) in order to display information regarding the speed of the batter/runner 36, as previously discussed.

It is to be further understood that each baseball base 26, 28, 30 and 32 can be equipped with a unique identifier to be used in wireless communication. For example, according to a master device 714 option, each baseball base 26, 28, 30 and 32 reports an event (such as the contacting of the batter/runner 36 with the base) to the master device 714 and master device 714 calculates time and speed based on reported base data received. As discussed above, the master device 714 has a precise clock 710 and all other devices just need to report the time events from the runner to the master device 714. It is to be further understood that the clock 710 resulting time stamps from any event are universal and synchronized with the official game time and video equipment to enable output reporting capabilities to all baseball park equipment, so in video playback it is possible to review the time that ball is caught by the player covering that particular base and compare this time to the base impact time of the batter/runner 36 instead of trying to review two different video feeds.

Another way that the unique identifier of each base that can be used wirelessly is through a hand over option. In this instance, the timing devices will, at least, hear and record data from the previous device and will start a precise local timer when the previous base signal is heard. This configuration allows for base running time and speed information to be calculated locally without a master device 714.

A still another way that the unique identifier of each base can be used wirelessly is through an independent timer option. In this manner, all of the baseball bases 26, 28, 30 and 32 hear each other. Each base 26, 28, 30 and 32 will start a timer for any base signal heard and report all events to the master device 714 so that the batter/runner 36 can access any base-to-base time period locally. It is to be understood that the events can be sent to a master device 714 for speed and time calculations or calculated locally at any base. Furthermore, data from the base modules 700 and 800 could be sent directly to a mobile device (not shown) either as purely a display device or the device to process the measurements and report the data (master device 714).

It is to be further understood that each baseball base 26, 28, 30 and 32 can be equipped with a unique identifier to be used in a wired communication. For example, each base 26, 28, 30 and 32 can be wired to a main processor (master device 714). In this instance, each base 26, 28, 30 and 32 transmits a base identifier so the master device 714 can calculate base-to-base time and speed. Furthermore, all of the bases 26, 28, 30 and 32 can be wired together in a bus configuration such that each base 26, 28, 30 and 32 is able to process data and display the base running time from any previous base signal using the unique base identifier given for each location (homeplate though $3^{rd}$ base). It is to be even further understood that the wired link can include power and communication links or a communication over power link, as is well known in the art. Finally, the bases could be wired to specific inputs on a master device 714 (inputs such as $1^{st}$ base, second base, etc.) in an effort to simplify the system and eliminate the need for specific addresses for each base.

Regarding the wired connection, as shown in FIG. 9, wired module 800 would be located in each base along with wired communication abilities to report base impact data to any other bases or modules to calculate a runner's time between bases. As shown in FIG. 9, wireless module 800, includes, in part, conventional touch/position sensor 802, conventional vibration sensor 804, a conventional crystal 810, a conventional microphone system 803, a conventional runner ID system (such as RFID) 805, and conventional microprocessor 812.

As can be seen in FIG. 8, touch/position sensor 802 and vibration sensor 804 are connected to microprocessor 812.

It is to be understood that wired module 800 would provide power, ground, and communication links 808 that are either extended out of the side of the base for a temporary install or run underground from each base and brought back to a central location (master device 714) for processing. Furthermore, wired module 800 may include a centralized panel (not shown) located on the backstop of the baseball field where all base wiring would be routed to. This panel may contain the central processing unit (master device 714) and all of the baseball bases 26, 28, 30 and 32 would be low cost sensors whose data merely gets sent to the master device 714 to be analyzed. Alternatively, the bases 26, 28, 30 and 32 could each have individual microprocessor capabilities and do all processing locally. This individual microprocessor capability applies to the wireless module 700, too. Finally, the wiring could be a single loop of wire starting at home plate 32, then first through third bases and returning to homeplate 32, or it could be individual wires to each base 26, 28, 30 and 32. The wiring would include a conventional communication bus (not shown) so that all bases 26, 28, 30 and 32 can communicate any data needed between the other base locations.

As is well known in the wired communications art, once the batter/runner 36 contacts or otherwise interacts with a base, the touch/position sensor 802 and/or vibration sensor 804 is activated and the signal is conventionally transmitted to the microprocessor 812. The microprocessor 812 is then used to transmit to master device 714 the timing data of the batter/runner 36 so that the speed and time of the batter/runner 36 can be calculated by the master device 714, as discussed above. Finally, the speed and time of the batter/runner is then transmitted to the display device (not shown) in order to display information regarding the speed of the batter/runner 36, as previously discussed.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein is a new and improved athletic speed timer. The preferred athletic speed timer, according to various embodiments of the present invention, offers the following advantages: ease of use; lightness in weight; durability; waterproof; dustproof; improved speed measurement characteristics; the ability to see the effect on the batter/runner's speed when touching an object such as a base in the game of baseball; the ability to accurately measure the entire time period from when the baseball hits the bat to the time the batter/runner touches the base(s) with his/her foot or other part of their body while sliding; the ability to accurately measure the time between the moment the batter/runner's contact leaves one base and touches the next; the ability to report the batter/runner's contact position/location on the base to provide data that could be used to reduce the running time; the ability to accurately detect the batter/runner's touch through the implementation of simple switch closures, vibration sensors, and/or touch sensors; the use of base touching timing and location data to aid with real game situations to show whether the fielder tagged the base before the batter/runner or vice versa; and the ability to keep track of a player's improvement in speed. In fact, in many of the preferred embodiments, these advantages of ease of use, lightness in weight, durability, waterproof, dustproof, improved speed measurement characteristics, the ability to see the effect on batter/runner's speed when touching an object such as a base in the game of baseball, the ability to accurately measure the entire time period from when the baseball hits the bat to the time the batter/runner touches the base(s), the ability to accurately measure the time between the moment the batter/runner's foot leaves one base and touches the next, the ability to report the batter/runner's foot position on the base to provide data that could be used to reduce the running time, the ability to accurately detect the runner's touch through the implementation of simple switch closures, vibration sensors and/or touch sensors, base touching timing and location data can be used to aid with real game situations to show whether the fielder tagged the base before the batter/runner or vice versa, and the ability to keep track of a player's improvement in speed are optimized to an extent that is considerably higher than heretofore achieved in prior, known athletic speed timers.

I claim:

1. An athletic speed and time measurement device, comprising:
a ball/bat impact detecting device located adjacent to a batter/runner, wherein the ball/bat impact detecting device detects an impact of a ball with a bat as the batter/runner swings the bat and contacts the bat with the ball, wherein the ball/bat impact detecting device further includes frequency content analysis that processes at least one frequency such that bat and ball strike frequency spectrums are processed and non-bat ball strike frequency spectrums are ignored; and
a batter/runner timing device, wherein the batter/runner timing device determines a difference in time between when the ball/bat impact detector detects the impact of the ball with the bat at a first of a plurality of bases and a contact detection device on a second of the plurality of bases detects that the batter/runner has contacted the second of the plurality of bases.

2. The athletic speed and time measurement device, as in claim 1, wherein the batter/runner contact detection device is further comprised of:
a RFID reader located adjacent to at least one of the plurality of bases, wherein the RFID reader registers an identification of the batter/runner.

3. The athletic speed and time measurement device, as in claim 1, wherein the batter/runner contact detection device is further comprised of:
a touch sensor operatively connected to each of the plurality of bases.

4. The athletic speed and time measurement device, as in claim 1, wherein the ball/bat impact detecting device is further comprised of:
at least one microphone operatively connected to the first of the plurality of bases.

5. The athletic speed and time measurement device, as in claim 1, wherein the ball/bat impact detecting device is further comprised of:
at least one microphone located adjacent to the first of the plurality of bases.

6. The athletic speed and time measurement device, as in claim 1, wherein the ball/bat impact detecting device is further comprised of:
at least one ball/bat impact detector operatively attached to the batter/runner.

7. The athletic speed and time measurement device, as in claim 1, wherein the ball/bat impact detecting device is further comprised of:
a batting tee with a ball/bat impact detector located adjacent to a location of the ball being held on the tee.

8. The athletic speed and time measurement device, as in claim 1, wherein the batter/runner timing device is further comprised of:
a mat located adjacent to the first of the plurality of bases, wherein the batter/runner timing device determines a difference in time between when the ball/bat impact detector detects the impact of the ball with the bat and a contact detection device on the mat detects that the batter/runner has left the mat.

9. An athletic speed and time measurement device for use during a sporting event, comprising:
a ball/bat impact detecting device located adjacent to a batter/runner, wherein the ball/bat impact detecting device detects an impact of a ball with a bat as the batter/runner swings the bat and contacts the bat with the ball, wherein the ball/bat impact detecting device further includes frequency content analysis that processes at least one frequency such that bat and ball strike frequency spectrums are processed and non-bat ball strike frequency spectrums are ignored; and
a batter/runner timing device, wherein the batter/runner timing device determines a difference in time between when the ball/bat impact detector detects the impact of the ball with the bat at a first of a plurality of bases and a contact detection device on a second of the plurality of bases detects that the batter/runner has contacted the second of the plurality of bases.

10. The athletic speed and time measurement device for use during a sporting event, as in claim 9, wherein the batter/runner contact detection device is further comprised of:
a vibration sensor operatively connected to each of the plurality of bases.

11. The athletic speed and time measurement device for use during a sporting event, as in claim 9, wherein the batter/runner contact detection device is further comprised of:
a touch sensor operatively connected to each of the plurality of bases.

12. The athletic speed and time measurement device for use during a sporting event, as in claim 9, wherein the ball/bat impact detecting device is further comprised of:
at least one ball/bat impact detector operatively attached to the batter/runner.

13. The athletic speed and time measurement device for use during a sporting event, as in claim 9, wherein the ball/bat impact detecting device is further comprised of:
a batting tee with a ball/bat impact detector located adjacent to a location of the ball being held on the tee.

14. The athletic speed and time measurement device for use during a sporting event, as in claim 9, wherein the batter/runner timing device is further comprised of:
a mat located adjacent to the first of the plurality of bases, wherein the batter/runner timing device determines a difference in time between when the ball/bat impact detector detects the impact of the ball with the bat and a contact detection device on the mat detects that the batter/runner has left the mat.

15. A method for measuring an athletic speed and time, comprising the steps of:
providing a ball/bat impact detecting device located adjacent to a batter/runner, wherein the ball/bat impact detecting device detects an impact of a ball with a bat as the batter/runner swings the bat and contacts the bat with the ball, wherein the ball/bat impact detecting device further includes frequency content analysis that processes at least one frequency such that bat and ball strike frequency spectrums are processed and non-bat ball strike frequency spectrums are ignored; and
providing a batter/runner timing device, wherein the batter/runner timing device determines a difference in time between when the be ball/bat impact detector detects the impact of the ball with the bat at a first of a plurality of bases and a contact detection device on a second of the plurality of bases detects that the batter/runner has contacted the second of the plurality of bases.

16. The method for measuring an athletic speed and time, as in claim 15, wherein the step of providing a batter/runner timing device is further comprised of the step of:
providing a vibration sensor operatively connected to each of the plurality of bases.

17. The method for measuring an athletic speed and time, as in claim 15, wherein the step of providing a batter/runner timing device is further comprised of the step of:
providing a touch sensor operatively connected to each of the plurality of bases.

18. The method for measuring an athletic speed and time, as in claim 15, wherein the step of providing a ball/bat impact detecting device is further comprised of the step of:
providing at least one microphone operatively connected to the first of the plurality of bases.

19. The method for measuring an athletic speed and time, as in claim 15, wherein the step of providing a ball/bat impact detecting device is further comprised of the step of:
providing at least one microphone located adjacent to the first of the plurality of bases.

20. The method for measuring an athletic speed and time, as in claim 15, wherein the step of providing a ball/bat impact detecting device is further comprised of the step of:
providing at least one ball/bat impact detector operatively attached to the batter/runner.

21. An athletic speed and time measurement device, comprising
a runner timing device, wherein the runner timing device determines a difference in time between when a first runner contact detection device located in a first of the plurality of bases detects that a runner has left the first of the plurality of bases and a second runner contact detection device located on a second of the plurality of bases detects that the runner has contacted the second of the plurality of bases, wherein the second runner contact detection device includes a runner contact force direction detector.

* * * * *